(12) United States Patent
Kullberg et al.

(10) Patent No.: US 10,083,506 B2
(45) Date of Patent: Sep. 25, 2018

(54) WHOLE BODY IMAGE REGISTRATION METHOD AND METHOD FOR ANALYZING IMAGES THEREOF

(71) Applicant: ANTAROS MEDICAL AB, Uppsala (SE)

(72) Inventors: Joel Kullberg, Uppsala (SE); Håkan Ahlström, Uppsala (SE); Robin Strand, Uppsala (SE)

(73) Assignee: ANTAROS MEDICAL AB, Uppsala (SE)

( * ) Notice: Subject to any disclaimer, the term of this patent is extended or adjusted under 35 U.S.C. 154(b) by 0 days.

(21) Appl. No.: 15/524,368

(22) PCT Filed: Nov. 6, 2015

(86) PCT No.: PCT/SE2015/051177
§ 371 (c)(1),
(2) Date: May 4, 2017

(87) PCT Pub. No.: WO2016/072926
PCT Pub. Date: May 12, 2016

(65) Prior Publication Data
US 2018/0144472 A1 May 24, 2018

(30) Foreign Application Priority Data

Nov. 7, 2014 (SE) .................... 14005375

(51) Int. Cl.
*G06T 7/00* (2017.01)
*A61B 5/00* (2006.01)
(Continued)

(52) U.S. Cl.
CPC ............ *G06T 7/0014* (2013.01); *A61B 5/055* (2013.01); *A61B 5/4504* (2013.01);
(Continued)

(58) Field of Classification Search
USPC .................................................. 382/128, 131
See application file for complete search history.

(56) References Cited

U.S. PATENT DOCUMENTS 7,876,938 B2 * 1/2011 Huang .................... G06T 7/174
382/128
8,139,830 B2 * 3/2012 Krishnan .................. G06T 7/33
382/128
(Continued)

FOREIGN PATENT DOCUMENTS

WO 2013/001399 A2 1/2013
WO 2013/121379 A2 8/2013

OTHER PUBLICATIONS

Hasegawa A. et al., A Tool for Temporal Comparison of Mammograms: Image Toggling and Dense-Tissue-Preserving Registration, International Workshop on Digital Mammography (IWDM), pp. 447-454 (2008).
(Continued)

*Primary Examiner* — Ishrat I Sherali
(74) *Attorney, Agent, or Firm* — Porter Wright Morris & Arthur LLP

(57) ABSTRACT

A method for registration of whole body volume images comprises obtaining (210) of a first image and a second image, comprising water and fat whole body magnetic resonance image data. Bone tissue are identified (220), creating respective bone images. Water components are separated (230), generating respective water images based on absolute water content. Fat components are separated (240), generating respective fat images based on absolute fat content. The first image is registered (250) to the second image by deforming the first bone image according to a bone tissue deformation rule, deforming the first water image according to a water tissue deformation rule under constraints of the first bone image deformation and deforming
(Continued)

the first fat image according to a fat tissue deformation rule under constraints of the first bone image and the deformation of said first water image. Also, a method for analyzing the registered images is provided.

20 Claims, 16 Drawing Sheets

(51) Int. Cl.
| | |
|---|---|
| *G06T 7/11* | (2017.01) |
| *G06T 7/33* | (2017.01) |
| *G01R 33/56* | (2006.01) |
| *A61B 5/055* | (2006.01) |
| *G01R 33/48* | (2006.01) |
| *A61B 90/00* | (2016.01) |

(52) U.S. Cl.
CPC .......... *A61B 5/4872* (2013.01); *A61B 5/4875* (2013.01); *A61B 5/7246* (2013.01); *G01R 33/5608* (2013.01); *G06T 7/11* (2017.01); *G06T 7/337* (2017.01); *A61B 2090/364* (2016.02); *A61B 2576/00* (2013.01); *G01R 33/4828* (2013.01); *G06T 2207/10088* (2013.01); *G06T 2207/20128* (2013.01); *G06T 2207/30008* (2013.01); *G06T 2207/30204* (2013.01)

(56) References Cited

U.S. PATENT DOCUMENTS

| | | | | |
|---|---|---|---|---|
| 8,237,441 | B2* | 8/2012 | Martinez-Moller | ... A61B 5/055 250/363.01 |
| 8,588,495 | B2 | 11/2013 | Gupta et al. | |
| 9,147,250 | B2* | 9/2015 | Liu | .................... G01R 33/5608 |
| 2006/0052686 | A1* | 3/2006 | Zhang | ....................... G06T 7/32 600/407 |
| 2010/0067769 | A1 | 3/2010 | Neemuchwala et al. | |
| 2013/0044927 | A1 | 2/2013 | Poole | |
| 2014/0270446 | A1 | 9/2014 | Vija | |
| 2014/0296696 | A1* | 10/2014 | Remmele | ........... G01R 33/4816 600/410 |
| 2016/0000384 | A1* | 1/2016 | Gall | ................. G01R 33/56358 600/413 |

OTHER PUBLICATIONS

Lelieveldt B.P.F. et al., Towards integrated analysis of longitudinal whole-body small animal imaging studies, International Conference on Acoustics, Speech and Signal Processing (ICASSP), pp. 5768-5771 (2011).

Maintz, J.B.A. et al., A survey of medical image registration, Medical Image Analysis, vol. 2, No. 1, pp. 1-37 (1998).

Bley T.A. et al., Fat and Water Magnetic Resonance Imaging, Journal of Magnetic Resonance Imaging, vol. 31, No. 1, pp. 4-18 (2010).

Karlsson et al., Automatic and Quantitative Assessment of Regional Muscle Volume by Multi-Atlas Segmentation Using Whole-Body Water-Fat MRI, Journal of Magnetic Resonance Imaging, p. 1-12 (online Aug. 11, 2014).

Joshi et al., Automatic Intra-Subject Registration-Based Segmentation of Abdominal Fat from Water-Fat MRI, Journal of Magnetic Resonance Imaging, 37:423-430 (Aug. 7, 2012).

Ashburner et al., Voxel-Based Morphometry—The Methods, NeuroImage, 11:805-821 (2000).

Aerts et al., Decoding tumour phenotype by noninvasive imaging using a quantitative radiomics approach, Nature Communications, p. 1-9 (online Jun. 3, 2014).

* cited by examiner

FIG. 15

51 — PERFORMING A COMPARISON OF WHERE AND HOW IMAGE FEATURES, OR IMAGE FEATURES DERIVED FROM A DEFORMATION FIELD, OF WHOLE BODIES DIFFER WITHIN A FIRST GROUP OF FIRST SETS OF VOLUME IMAGES AND WITHIN A SECOND GROUP OF FIRST SETS OF VOLUME IMAGES ARE COMPRISED WITHIN AN ATLAS OF VOLUME IMAGES

52 — CALCULATING A CORRELATION BETWEEN IMAGE FEATURES, OR IMAGE FEATURES DERIVED FROM A DEFORMATION FIELD, OF A GROUP OF FIRST SETS OF VOLUME IMAGES OF WHOLE BODIES OF THE VOLUME IMAGE ATLAS AND COLLECTED NON-IMAGING DATA ASSOCIATED WITH SAID WHOLE BODIES COMPRISING ONE OR MORE OF: BLOOD PRESSURE OR MEASUREMENT RESULTS FROM BLOOD ANALYSIS, MEASUREMENT RESULTS FROM NON-IMAGING ANALYSIS, BIOMARKERS OR DATA FROM LONGITUDINAL STUDIES OF DISEASE DEVELOPMENT

53 — PERFORMING A COMPARISON OF IMAGE FEATURES, OR IMAGE FEATURES DERIVED FROM A EFORMATION FIELD, FROM A SET OF REGISTERED VOLUME IMAGES OF A WHOLE BODY AND A VOLUME IMAGE ATLAS OF REGISTERED VOLUME IMAGES OF MULTIPLE WHOLE BODIES, ENABLINGDETECTING WHERE AND HOW IMAGE FEATURES FROM A WHOLE BODY DEVIATE FROM IMAGE FEATURES FROM MULTIPLE BODIES OF THE ATLAS OF VOLUME IMAGES

54 — USING THE METHOD FOR REGISTRATION OF VOLUME IMAGES TO IDENTIFY BONE TISSUE AND AT LEAST ONE OTHER TISSUE OF THE VOLUME IMAGES, ENABLING TISSUE QUANTIFICATION IN MR-TYPE IMAGING IMPROVING ATTENUATIONCORRECTION IN PET-MR IMAGING

55 — PERFORMING COMPARISONS OF WHERE AND HOW IMAGE FEATURES DIFFER BETWEEN SETS OF REGISTERED VOLUME IMAGES OF ONE AND THE SAME WHOLE BODY, ACQUIRED AT DIFFERENT TIME POINTS

WHOLE BODY IMAGE REGISTRATION METHOD AND METHOD FOR ANALYZING IMAGES THEREOF

TECHNICAL FIELD

This disclosure relates to image registration. In particular it provides a method for whole body image registration and a method for analyzing images.

BACKGROUND

In medical imaging, information being collected is typically reduced to a few measured parameters subsequent to state of the art image processing. These measured parameters may for example include subcutaneous fat volume, visceral fat volume, muscle volume, tumor diameter, and liver fat content. Information from imaging comprising millions of measurement samples is often reduced to a few output parameter values.

Imaging applications are typically designed to provide answers to questions concerning one or more a priori determined target parameters, for example fat volume or tumor diameter. This is typically achieved by gross filtering of image information resulting in a large data reduction.

Traditional whole body image analysis approaches provide a few measures from images analyzed separately.

In neuroimaging, statistical parameter mapping (SPM) and voxel based morphometry (VBM) are concepts for processing of magnetic resonance imaging (MRI) image data of brain only, (Ref. 1). By using image registration using a common standardized volume and performing segmentation of different tissues, such as grey matter and white matter, group comparisons and correlation analysis can be performed by statistics on morphological or functional data. The registration methods used herein are not stable enough to be suitable for whole body images.

In radiomics, a feature analysis of pre-segmented regions can be made (Ref. 2). This is an initiative to use radiology medical imaging to monitor the development and progression of cancer or its response to therapy providing a comprehensive quantification of a tumor phenotype. Radiomics enables high-throughput extraction of a large amount of quantitative features from radiology medical images of a given modality, such as computed tomography (CT), positron emission tomography (PET), and MR, and can provide complementary and interchangeable information compared to sources such as demographics, pathology, blood biomarkers, or genomics, improving individualized treatment selection and monitoring. The statistical analysis is radiomics is restricted to pre-defined, pre-segmented regions of the images, only.

Gupta et al. (Ref. 3) presented a method for building a statistical whole-body atlas using pre-segmented objects, landmarks, by generative or discriminative learning methods. However, the statistical analysis on non-imaging (meta) data, voxel intensities, statistics on global and local shape deformations or statistics on joint articulations is limited to analyzing one volume at the time of the atlas. However, such atlases are not based on fat and/or water MR images.

Moreover, a statistical atlas on texture features as well as a method for voxel-wise multivariate analysis thereof, is known from Poole (Ref. 4), focusing on brain images. By determining a measure of the difference between image data and the statistical atlas, the presence of abnormality can be determined. Analysis of a whole body is mentioned, but stated to be 'too difficult to achieve'. The statistical analyzes enabled seem to be limited to comparisons of one image with many other images.

Also, multi-band registration of water-fat MRI images has been used for segmentation of abdominal fat from water-fat MRI images (Ref. 5). A multi-band method that utilizes signal from both fat and water images is used to register the abdominal water-fat MRI images. This abdominal MRI images are obviously restricted to the abdomen, which is a disadvantage.

In addition, a method for registration of whole-body water-fat MRI images has been applied to segmentation and quantification of abdominal fat and to muscle quantification (Ref. 6). This registration method is unavoidably sensitive to noise and acquisition artefacts, as it does not utilize pre-computed features. Image registration herein is limited to one band, being water image only. Since one band is used only tissue specific features are used herein. Although comparisons between images are performed (multi-atlas approach), implicitly comprising some adaptation of an image, such adaptation is not explicitly taken advantage of in studies presented. A statistical analysis is carried out on pre-defined regions only.

In the published US patent application US 2014/0270446 A1, a method and apparatus for registration of multimodal imaging data using constraints are disclosed. The object image is segmented into one or more anatomic segments, being identified organs or tissues, associated with an anatomic class. A registration is performed constrained by assigned attributes.

A survey of medical image registration techniques is presented by J. B. A. Maintz and M. A. Viergever in "A survey of medical image registration", in Medical Image Analysis (1998) vol. 2, No. 1, pp. 1-36.

The methods as described above are either focused on too small a region of interest, or use a limited number of bands or images, which restricts the resolution and the accuracy of any possible analyzes of registered images.

There is therefore a need for an improved image registering method, by which at least some of the issues outlined above are addressed.

SUMMARY

It is an object of the proposed technology to provide a robust whole body image registration method enabling analyzing of whole body images. The above object is achieved by methods and devices according to the independent claims. Preferred embodiments are defined in dependent claims.

In general words, in a first aspect, a method for registration of whole body volume images comprises obtaining a first image and a second image. The first image is a whole body volume image comprising water and fat magnetic resonance image data and the second image is a whole body volume image comprising water and fat magnetic resonance image data. Bone tissue is identified from the first image creating a first bone image, and bone tissue is identified from the second image creating a second bone image. Water componentsare separated from the first image, generating a first water image based on absolute water content, and water components are separated from the second image, generating a second water image based on absolute water content. Fat components are separated from the first image, generating a first fat image based on absolute fat content, and fat components are separated from the second image, generating a second fat image based on absolute fat content. The first image is registered to the second image by deforming the first bone image according to a bone tissue deformation rule, deforming the first water image according to a water tissue deformation rule under constraints of the deformation of the first bone image and deforming the first fat image according to a fat tissue deformation rule under constraints of the deformation of the first bone image and the deformation of the first water image.

In a second aspect, a method for analysis of whole body volume images comprises analysing image features of whole body volume images obtainable by a registering method according to the first aspect in a holistic manner. The image features comprises one or more of signal intensities, features derived from a deformation field, and filtered measures derived from imaging parameters and optionally also from non-imaging parameters in all voxels.

Embodiments of the present invention carry a number of advantages.

One advantage with the proposed technology is that it provides an enhanced quality of image registration achieved by use of tissue-dependent registration rules. Thereby, a holistic analysis approach anywhere in a body allowing statistical analysis and integration of imaging and non-imaging data is enabled. Correlations performed between image data from any region and non-imaging data of the body studied are enabled.

Other advantages will be appreciated when reading the detailed description.

BRIEF DESCRIPTION OF THE DRAWINGS

Embodiments will now be described in more detail, and with reference to the accompanying drawings, in which:

FIG. 15 schematically illustrates a method for image analysis; and

DETAILED DESCRIPTION

Figure 1:
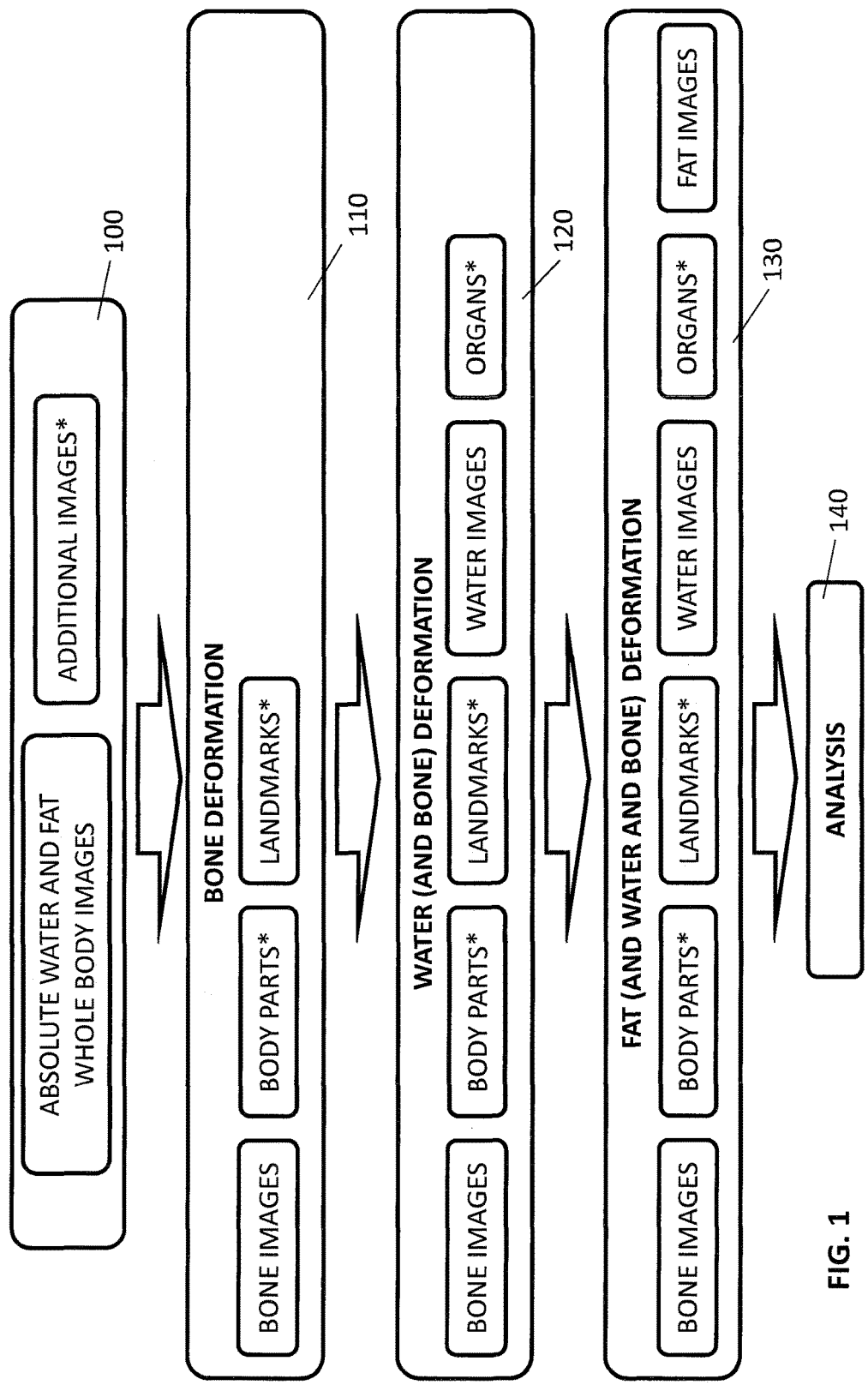
FIG. 1 illustrates an embodiment of registration and analysis.

In the following description, different embodiments of the invention will be described in more detail, with reference to accompanying drawings. For the purpose of explanation and not limitation, specific details are set forth, such as particular examples and techniques in order to provide a thorough understanding.

Throughout the drawings, the same reference numbers are used for similar or corresponding elements. Furthermore objects in drawings denoted with (*) are optional.

In all illustrated whole body images, except 610, 611, 620, the images are represented by coronal example slices.

It should be mentioned that imaging of whole bodies and whole-body imaging is herein to be understood as bodies or imaging of bodies, respectively, comprising at least the thoracic, abdominal and pelvic regions.

The intensity average and shape information average as mentioned herein are to be understood as general mean values of two or more intensity and shape information values, respectively, of a distribution of values.

This disclosure aims at using image data to a higher degree and/or in a more efficient manner than in prior art, involving statistical analysis of image features using all image data that allows integration of non-imaging data into an image analysis. This approach is related to other well-established omics-concepts such as Genomics, Proteomics, Metabolomics and, Lipidomics.

It has been found that image registration, i.e. the process in which a first image is deformed to match a second image that is fixed, is crucial for a statistical comparison of whole-body images when bodies or objects that are studied are not pre-segmented.

Indeed, even in cases in which studied bodies or objects are pre-segmented an improved registration may be of benefit.

It is emphasized that the application of statistics requires that the image data or images, in short, lies aligned in relation to each other in the same space, i.e. the images have to be registered. Accurate and precise image registration is crucial e.g. for building a high-quality statistical atlas.

When targeting whole body images and analysis thereof, it is important to find a robust registering approach, being applicable to essentially the entire body. When registering has to rely on identification of particular organs, a robust registration is only obtainable in the vicinity of that organ. Registration of bone structure is a good beginning, since the bones are present throughout the entire body. Furthermore, except for the spinal column, bones are essentially rigid.

According to the proposed technology, instead of focusing on organs, the registration process instead starts from the insight that tissues throughout the entire body can be classified according to their deformation properties. Bone is one example, where a very limited degree of elasticity is allowed. For the remaining parts of the body, it can be assigned as predominantly water-containing or pre-dominantly fat-containing. Water-containing tissues have very similar deformation properties, regardless of which organs they belong to. Similarly, fat-containing tissues also have very similar deformation properties, but different from the water-containing tissues. By utilizing such similarities in deformation properties, registration of basically all parts of a body can be performed with a high degree of robustness.

In other words, different tissue are registered based on their morphological variation, starting with the tissue with lowest shape variation, bone.

Magnetic resonance imaging (MRI) allows imaging and quantification of many properties of human anatomy and physiology, such as morphology, diffusion, perfusion, regional brain tissue activation, etc. Separation of the fat- and water-components from the MRI signal can also be used to generate images that hold absolute fat- and water-content. By quantify the water and fat content in absolute values, tissues being pre-dominantly water-containing or fat-containing can be distinguished.

It can be noticed that in ref. 3, tissue-specific features are not considered and the methods to analyze are therefore primarily not based on image registration, for which reason statistical analysis is limited. Furthermore, in ref. 5, tissue-specific features are also not utilized herein and the statistical analysis is limited to pre-defined regions of the abdomen.

FIG. 1 illustrates an embodiment of registration and analysis. The description is held on an overview level, in order to provide an understanding of the underlying technology.

Water and fat whole body magnetic resonance (MR) images are provided in box 100. Absolute water and fat content are used. As will be discussed further below, additional images may also be provided, as well as non-imaging quantities.

In box 110, bone deformation is illustrated. The bone deformation is based on bone images. Optionally, a division into body parts is made. Also, optionally, a number of identified landmarks can be utilized.

In box 120, water deformation is illustrated. The water deformation is based on water images under constraints of the deformation of the bone image. Optionally, body parts, landmarks and/or identified organs are utilized.

In box 130, fat deformation is illustrated. The fat deformation is based on water images under constraints of the deformation of the bone image and the water image. Optionally, body parts, landmarks and/or identified organs are utilized.

In particular embodiments, the bone, water and/or fat deformation can be performed at least partly simultaneously and/or intermittently.

In box 140, the registered images are used for analysis.

Figure 2:
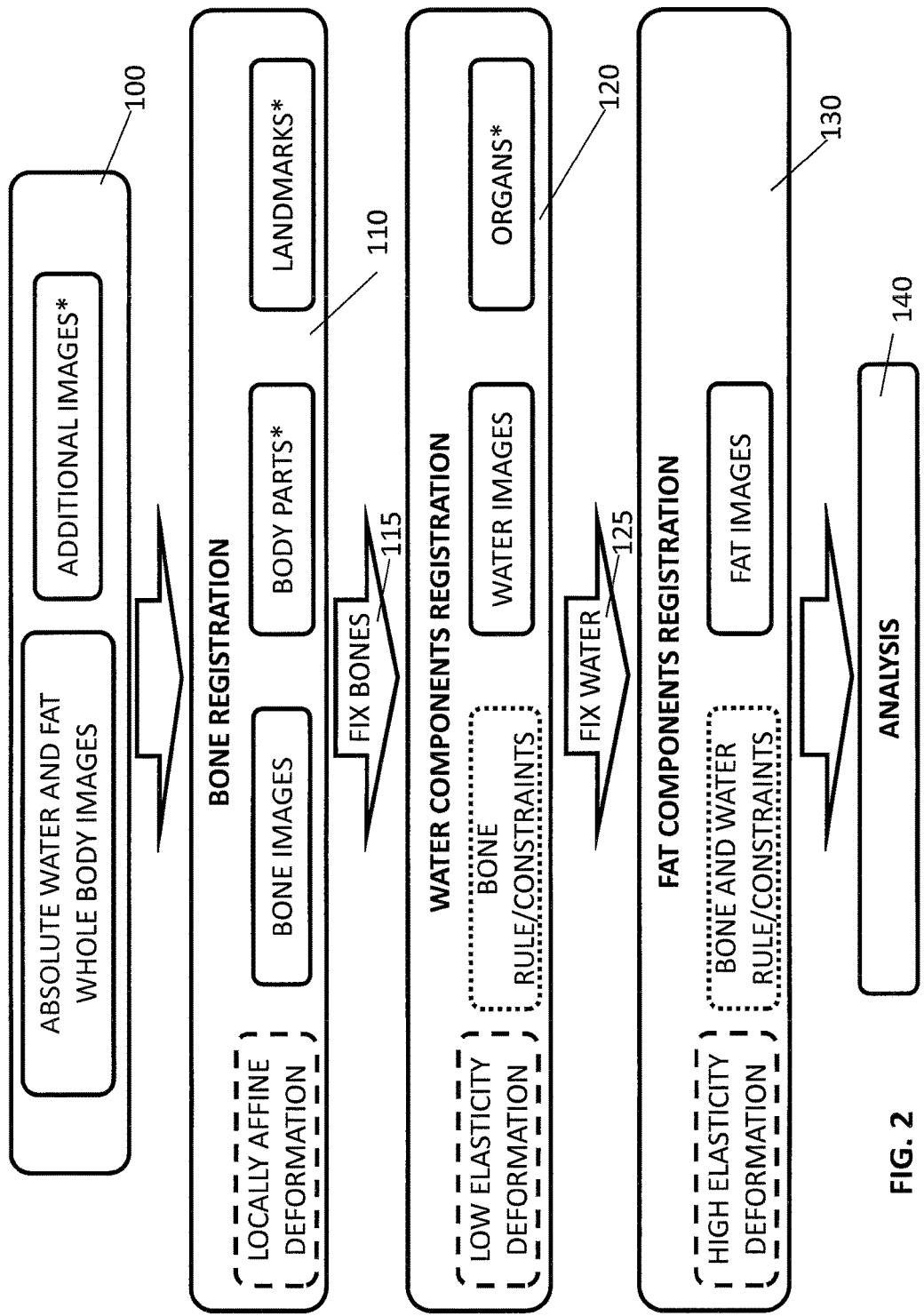
FIG. 2 illustrates another embodiment of registration and analysis.

FIG. 2 illustrates another embodiment of registration and analysis. Water and fat whole body magnetic resonance (MR) images, and optionally additional images, are provided in the box 100.

The provided images may in this embodiment be registered by firstly conducting bone registration 110. In bone registration, a locally affine deformation may be conducted based on information of bone images and optionally of body parts. Optionally, also landmarks may be used in said bone registration. The addition of landmarks, for example, foot, knee, hip and shoulder and/or shoulder landmarks typically adds robustness to the registration of body parts in whole body images.

Having bone registered, bone is fixed 115 for subsequent water and fat registration. Water registration 120 is secondly conducted. In water registration, a first elasticity deformation, with a, compared to fat, low elasticity, is conducted based on information from water images, with the fixed bones as constraints. Optionally, organs may be used in said water registration. The addition of organs adds robustness to registration in abdominal region in whole body images. The first elasticity is typically an elasticity being lower than an elasticity threshold.

Once water is registered, said registered water is fixed 125 for the subsequent fat registration. Similarly, fat registration 130 is thirdly conducted using the bone and water constraints. In fat registration, a second elasticity deformation, with a, compared to water, high elasticity, is conducted based on information from fat images, with the fixed bones and water as constraints. The second elasticity is typically higher than an elasticity threshold.

Analysis 140 of registered images are considered to be holistic, for the reasons of that a whole body is analyzed, that all or substantially all image data of provided images can be used in the analysis, and that an integration of non-imaging patient information is enabled in the analysis.

Figure 3:
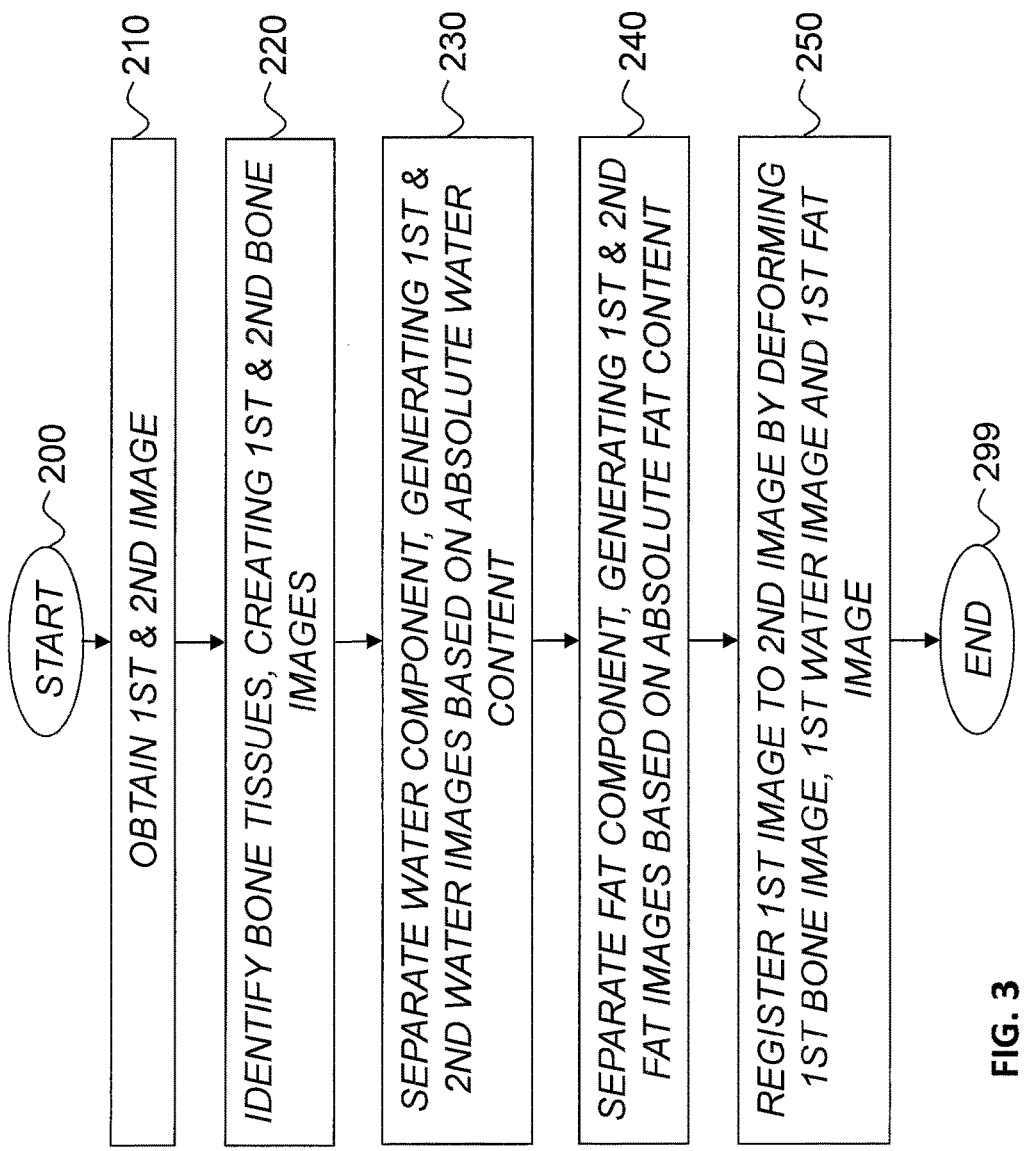
FIG. 3 is a flow diagram of steps of an embodiment of a method for registration of whole body volume images.

FIG. 3 illustrates a flow diagram of steps of an embodiment of a method for registration of whole body volume images. The method starts in step 200. In step 210, a first image and a second image are obtained. The first image is a whole body volume image comprising water and fat magnetic resonance image data. Also the second image is a whole body volume image comprising water and fat magnetic resonance image data. In step 220, bone tissue is identified from the first image creating a first bone image. Likewise, bone tissue is identified from the second image creating a second bone image. In step 230, water components are separated from the first image, generating a first water image based on absolute water content. Also, water components are separated from the second image, generating a second water image based on absolute water content. In step 240, fat components are separated from the first image, generating a first fat image based on absolute fat content. Also, fat components are separated from the second image, generating a second fat image based on absolute fat content. In step 250, the first image is registered to the second image by deforming the first bone image according to a bone tissue deformation rule, deforming the first water image according to a water tissue deformation rule under constraints of the deformation of the first bone image and deforming the first fat image according to a fat tissue deformation rule under constraints of the deformation of the first bone image and the deformation of the first water image. The procedure ends in step 299.

In a preferred embodiment, the bone tissue deformation rule comprises a bone tissue elasticity, the water tissue deformation rule comprises a water-containing tissue elasticity and the fat tissue deformation rule comprises a fat-containing tissue elasticity. The bone tissue elasticity is lower than the water-containing tissue elasticity and the water-containing tissue elasticity is lower than the fat-containing tissue elasticity.

In a preferred embodiment, the deforming of the first bone image is performed prior to the deforming of the first water image, and the deforming of the first water image is performed prior to the deforming of the first fat image.

In an alternative embodiment, the deforming of the first bone image, the first water image and the first fat image may be performed in a common process. The deformations may thus be performed at least partially simultaneous or interleaved.

In one embodiment, registering said first volume image, or in a more extended case one or more of a first set of volume images, onto the second volume image, or in the more extended case the second set of volume images, comprises determining point-to-point correspondences between the first image and the second image.

The first and second volume images within the method comprise images of at least one whole body.

Figure 4:
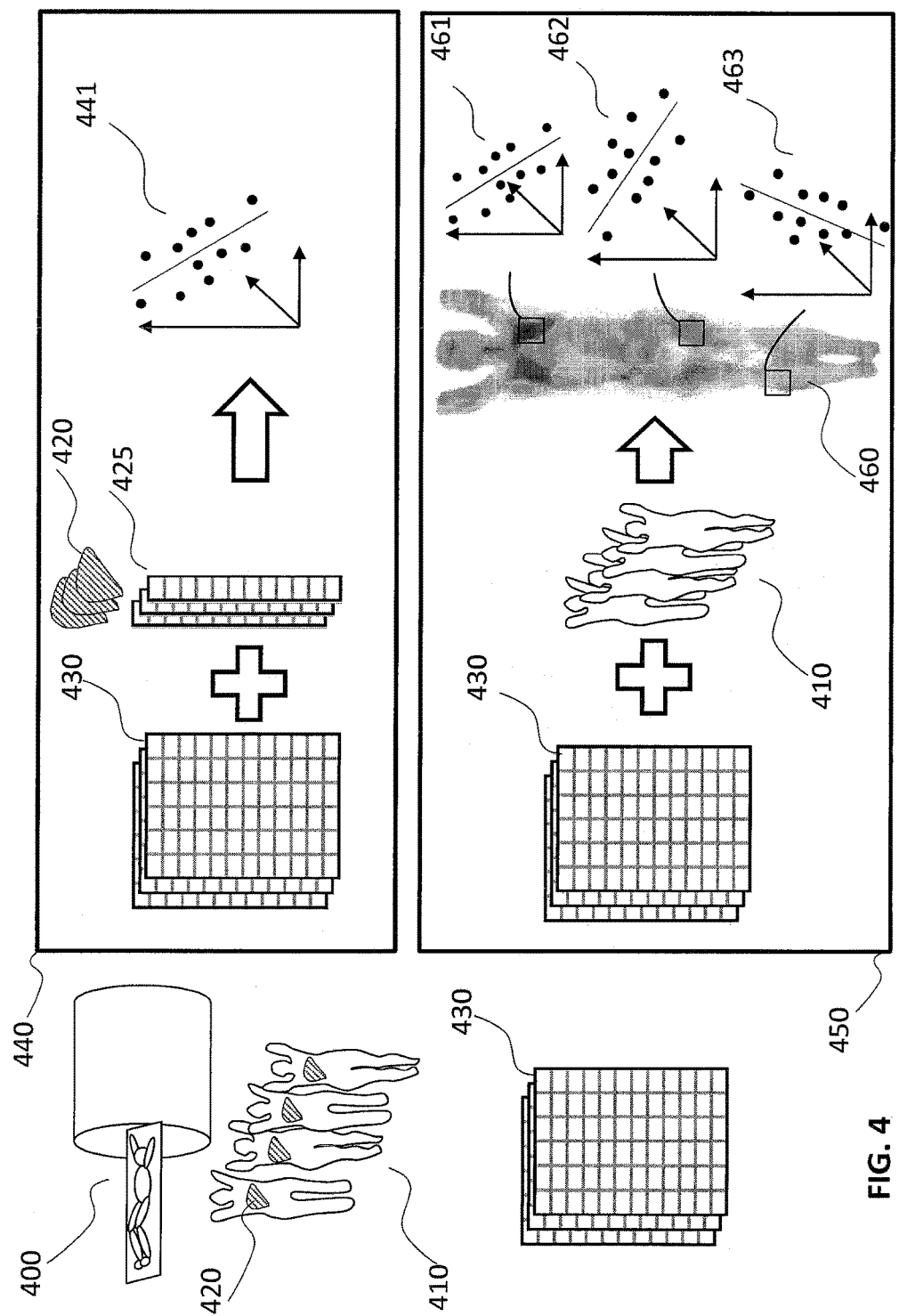
FIG. 4 illustrates differences between a standard analysis methods and the one enabled by the present disclosure.

FIG. 4 illustrates in a schematic manner differences between a standard prior-art analysis method and an embodiment of a method for analyzing images, according to the present disclosure.

A cohort of people 410, e.g. groups of healthy and/or non-healthy persons is investigated by different acquisition techniques. Imaging techniques 400 give raw image data from all subjects in the cohort 410. An explicit measurement of the liver 420 from the images is illustrated and results in the measurements illustrated as 425. Non-imaging techniques give typically one or several values of specified quantities, as raw data 430, also from all subjects in the cohort. When using standard analysis methods, as illustrated in 440 explicit measurements 425, such as e.g. a measurement from the liver 420, can be analyzed, possibly together with non-imaging data. This analysis typically gives rise to one or a few values of specified quantities. Irrespective of the quality of such analysis, the total available information in the image data is considerably reduced. A correlation between measurements from imaging data and non-imaging data is illustrated 441. Correlations may then be performed between the limited data deduced from the image data from liver and non-imaging data measured on the same body that was carrying the liver. Conclusions can thereby be drawn about correlations between the different discrete data sources.

By instead using the here presented technology, image data from all subjects of a whole body is integrated in the image analysis, as illustrated in 450. In the registration procedure, there is no reduction of data, and any information comprised in the original data is still present in the registered images. Statistical analysis may therefore be performed in the whole body region 460-463. Correlations may thus be performed between image data from any region and also including non-imaging data of the body studied.

As noticed above, magnetic resonance imaging (MRI) allows imaging and quantification of many properties of human anatomy and physiology, such as morphology, diffusion, perfusion, regional brain tissue activation, etc.

Fat and water components can be separated from the MRI signals to generate images that hold absolute fat and water content. In a preferred embodiment, the absolute fat content is defined as f/(f+w), where f is the fat signal amplitude and w is the water signal amplitude (real or complex). Analogously, the absolute water content is defined as w/(f+w). Such definitions are known, as such, in prior art, and are therefore not further discussed.

Optionally, additional images may be provided such as other types of MR-images and/or positron emission tomography (PET) images of different PET-tracers. The other types of MR images may comprise diffusion weighted or apparent diffusion coefficient (ADC) MR-images. The PET images may comprise fluorodeoxyglucose (FDG) images. The use of additional images, may improve identification of fat and water tissue or other tissue in images being registered. It may also improve registering of images to a common reference. Also, the inclusion of image features of the additional images may also improve an analysis of registered images.

Positron emission tomography (PET) offers a huge number of tracers and methods to study human physiology and function. Combined PET-MR scanners allow simultaneous collection and combination of all these measures in vivo with relatively low ionizing radiation exposure.

In other words, each set of volume images within the method may further comprise one or more types of MR images comprising: diffusion weighted MR images, ADC MR images, ultra-short echo time MR images, and zero echo time MR images.

Furthermore, in other words, each set of volume images within the method may further comprise one or more types of PET images, comprising static and dynamic FDG images.

It can be mentioned that medical imaging collects huge amounts of information. A 5 minutes whole-body MRI scan alone generates roughly 2003=8 million pixels. This corresponds to 8 million measurements of fat and water content. PET image data collected has lower resolution than MR. However, it still adds significantly to the amount of available image data and to an analysis of registered images.

It should be emphasized that embodiments of the present disclosure allow not only signal intensity from MRI or PET images to be compared. Also, fusion of image data will also cause different regions of a subject (whole body) to expand/contract and this can be used to estimate deviations in local volumes, of for example abdominal fat, muscles or liver, and also local deformations. Multiple local feature/texture measures, such as intensity heterogeneity may also be measured, which can be used to determine deviations of tissue heterogeneity, for example due to pathologies such as tumors or fibrosis.

Some examples of image features that can be included in an image analysis comprise signal intensities indicating fat content, diffusion, tracer uptake, etc., regional volumes of adipose tissue, muscle, liver, tumor, etc., and filtered measures such as texture, segmented tissues, for example fat depots/liver/lungs/bone, etc.

The here presented technology provides a method that can use the full potential of image data, since the image data is neither reduced to a few parameters or measures, nor is the analysis of which, separately analyzed. This enables a statistical analysis of image data from a large number of images.

In particular embodiments, the step of registering comprises determining of a volume deformation field and applying of the volume deformation field on the first volume image. This can be applied in general case, but will be discussed more in detail in connection with detailed embodiments presented here below. Thus, the following paragraphs present embodiments of deformation of volume images in a somewhat more detailed manner.

Detailed analysis within this disclosure rely on accurate and precise tissue-to-tissue, organ-to-organ, and point-to-point correspondences. Therefore, volume images are aligned in a reference coordinate system. Image registration relates to the problem of finding a displacement that spatially aligns a moving or movable image to a fixed image.

One output of image registration is also a so called deformation field; a vector field that defines to what position each point in the moving image should be mapped. In addition, to facilitate the alignment of the two images, the vector field holds information on local expansion, contraction, rotation, etc., that can be utilized in subsequent analysis steps. In other words, deforming bone tissue and water tissue and fat tissue may comprise determining of a volume deformation field and applying of that volume deformation field on the first image.

An image is a mapping $I:\Omega \rightarrow \mathbb{R}$, where $\Omega \subset \mathbb{Z}^3$. In image registration, a transformation $T(x)=x+u(x)$ that makes a deformed moving (target) image $I_M(T(x))$ spatially aligned to the fixed (reference) image $I_F(x)$ is sought.

The transformation is typically in many particular embodiments computed by minimizing a cost function. The cost function can for example be sum of squared intensity differences, mutual information or correlation. In general, the image registration of whole-body water and fat MRI volumes requires composition of multiple transformations, i.e., $T=T^n \circ T^{n-1} \circ \cdots \circ T^1$.

Image registration can be either parametric using for example B-splines, thin-plate splines or wavelets, or non-parametric, for example Demons or Morphons. The transform T can also be restricted to rigid or affine transformations.

In general, restrictions on the deformation field are needed in order to see to that the deformation field is, for example, smooth, invertible, or diffeomorphic and to avoid unexpected deformations. The parametric approach typically involves an implicit regularization since the parametric representation allows only smooth deformations. In an iterative non-parametric registration process $T_i(x)=x+u_i(x)$, the regularization can be obtained by, in each iteration, smoothing the deformation field $T_i(x)$ or the update deformation field $u_i(x)$.

Moreover, in order to improve efficiency and robustness and to avoid local minima, an image registration is usually carried out in different scales, starting from a coarse scale where the overall shape is first aligned. In the final step, fine-scale structures are aligned. This multiscale approach can be realized by using for example, Gaussian scale space and/or pyramid representations of the image data.

Except for the multiscale approach, several techniques are herein presented in order to speed up the demanding computations carried out in a registration process. Examples of such techniques are:

Stochastic subsampling, where the cost function is not computed based on the full image data, but on a random subset of the data;

Graphical processing unit (GPU) programming, where at least some of the computations are carried on the GPU instead of the central processing unit (CPU), can be used to speed up the computations.

The image registration method as presented in this particular embodiment comprises:

Articulated, piece-wise affine, registration of bone sections;

Registration of water images with constraints on bone; and

Registration of fat images with constraints on bone and water.

In an example solution, a variational approach to image registration may be used. This means that the deformation field may be achieved by energy minimization of a metric, i.e., weighted terms of energy functions and regularization terms. Essential steps in a variational approach to image registration are choice of metric, parameterization of the deformation field, optimization method to find the optimal parameters and interpolation methods. Obviously, deformable image registration is needed due to the high degree of morphological variability in whole-body images.

In a deformable registration, the deformation fields may be parameterized by, for example, a B-spline representation.

An optimization problem to be solved can be written $$\hat{T}_\mu = \underset{T_\mu}{\mathrm{argmin}} C(T, I_F, I_M),$$

where $C(T, I_F, I_M) = \underbrace{S(T, I_F, I_M)}_{\text{cost function}} + \underbrace{\gamma P(T)}_{\text{regularization}}.$ A stochastic gradient descent optimization method may be used due to its computational efficiency. To get a stable optimization process, a multi-resolution approach based on spatial down-sampling and Gaussian scale-space may also be used.

Cost functions S used in this embodiment comprise:
Sum of squared differences (SDD)
Landmark term: Anatomical landmarks can be used to guide the registration process. Here, the mean Euclidean distance error between landmarks in the fixed and moving images may be used.
Multi-band cost function: To allow multiple image input, a cost function that can handle multiple images may be needed. Here, this can be accomplished by using the following form of the cost function:

$$S(T, I_F, I_M) = \frac{1}{\sum_{i=1}^{N} \omega_i} \sum_{i=1}^{N} \omega_i S(T, I_F^i, I_M^i).$$

In particular embodiments, the method for registration of whole body volume images thus comprises the further step of identifying of a plurality of landmarks in the first image and in the second image. The step of registering thereby comprises matching of the identified plurality of landmarks between the first image and the second image. This can be applied in general case, but will be discussed more in detail in connection with detailed embodiments presented further below.

In a general view, anatomical landmarks may be used to guide the registration process. The anatomical landmarks may be obtained manually by a user or in an automated way by processing the image data that is used to achieve an initial, affine, deformation. The anatomical landmarks may also be used to guide the registration process by including information on point-to-point correspondences. In other words, in a particular embodiment, identifying bone tissue and water-containing tissue and fat-containing tissue of the first and second images may comprise identifying of landmarks of the first and the second images, and/or segmenting the water-containing tissue and/or the fat-containing tissue of the first and the second images. Registering the first image may comprise matching of the landmarks of the first image onto the landmarks of the second image.

In particular embodiments, the method for registration of whole body volume images comprises the further step of segmenting the first image and the second image into segments, wherein the step of registering is performed for each segment. In other words, the registering thus comprises matching of said segments between said first image and said second image. In a further embodiment, the step of segmenting the first image and saheid second image is performed in the first water image and the second water image, identifying organs. This can be applied in general case, but will be discussed more in detail in connection with detailed embodiments presented here below.

In particular embodiments, the method for registration of whole body volume images comprises extracting of a body mask from the water and fat magnetic resonance image data and extracting of body parts from the body mask. The step of registering is then performed for each of these body parts. This can be applied in general case, but will be discussed more in detail in connection with detailed embodiments presented further below.

Returning to the particular detailed example, as input data, MRI images with absolute fat and water content, denoted $I_{FAT}$ and $I_{WATER}$, and body mask, denoted $I_{BODY}$, may be used.

Figure 5:
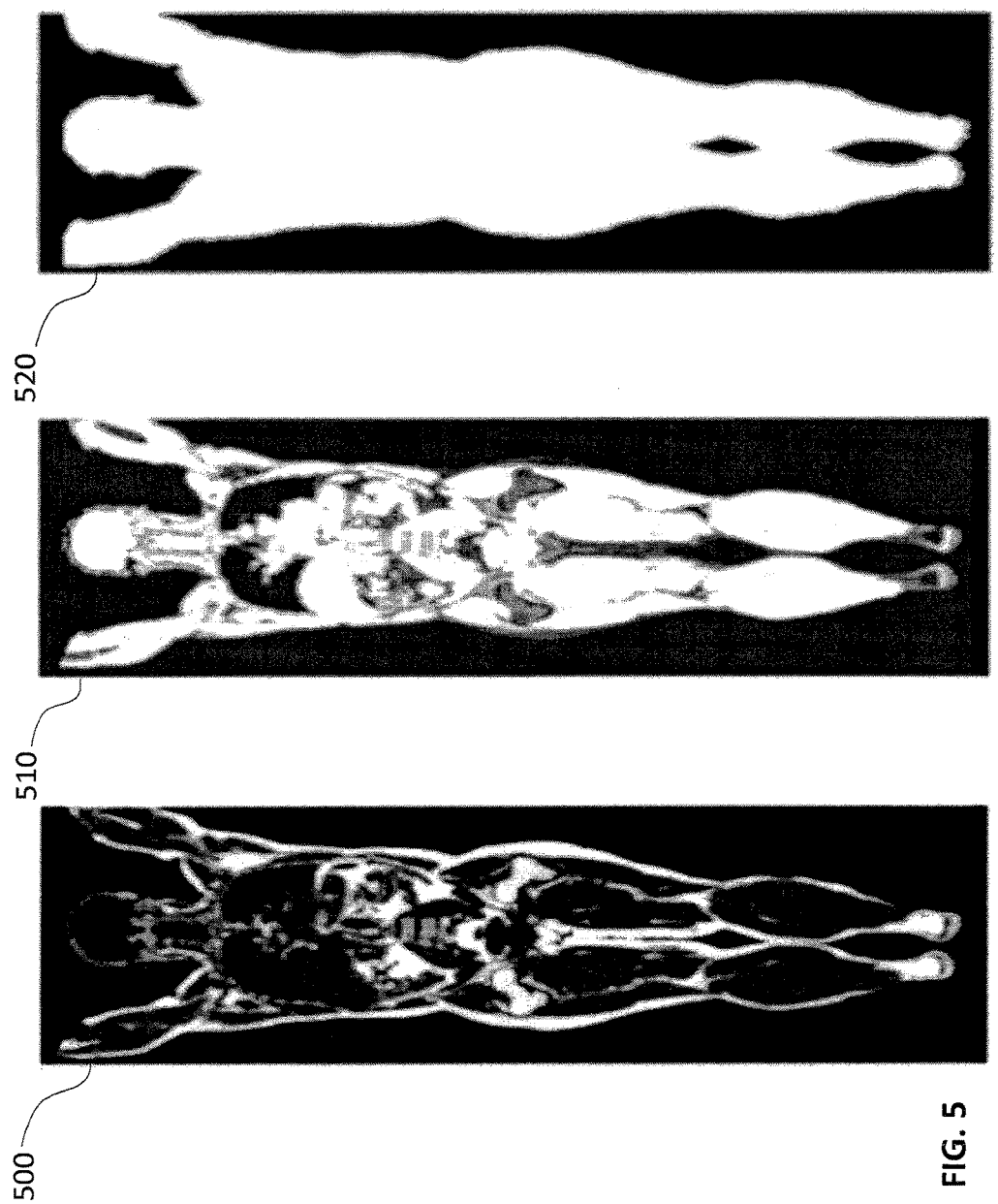
FIG. 5 presents examples of input image data and body mask.

FIG. 5 illustrates absolute fat 500, absolute water 510 and body mask 520 images which may be used as input image data. These images are coronal example slices.

A body mask 520 can typically be extracted from the image data. In an example implementation, this may be obtained by using intensity thresholds followed by morphological operations and region growing. From the body mask, separate sub regions may be extracted, for example arms, head, abdomen, and legs. In one implementation, this may be obtained by morphological analysis of the image data.

These ideas of segmentation can be utilized also in a general case. In other words, registering the first image may comprise registering the first image based on segmentation of the water-containing tissue of the first and the second images.

The whole-body sub regions may be used in the registration process to divide bone into corresponding sub regions, hereafter denoted bone sections. The bone sections may be deformed by separate affine transformations.

A rough segmentation of the skeleton can be computed by extracting regions with low signal in water and fat separated MRI, since air and bone do not produce any signal in water/fat separated MRI. From this, a segmented skeleton may be obtained by removing segmented lung and abdomen and by utilizing filtering techniques.

The first image may be a member of a first set of volume images to be registered, which set comprises one or more volume images. The first set of volume images may be volume images of one and the same whole body. The second image may be a volume image composed from one or more whole bodies. The second image may comprise intensity average and shape information average volume images based on volume images of multiple bodies.

In an example solution, the inter-individual morphological variation in bone, lean tissue (water signal), and adipose tissue (fat signal) may be assumed to be relatively low, medium and high, respectively. The example solution may divide the image registration process into three different steps, where different tissue are registered based on their morphological variation, starting with the tissue with lowest shape variation, bone.

The cost functions used in the individual steps of the registration procedure may be weighted sums of cost functions denoted $S_i$. As input to the cost functions may either be a moving image ($I_M$) and a fixed image ($I_F$) or sets of landmarks. Cost functions used in the different steps are described below.

Input data to the bone registration may comprise:
Eight landmarks: ankle joints, knees, hip joints, shoulder joints;
Segmented bone; and
Nine body parts: lower legs, upper legs, pelvis, torso, head, upper arms.
An example of body parts, bone sections and landmarks could be according to the following. Nine body parts, left and right lower and upper legs, pelvis, torso, head, and left and right upper arms, are used. These body parts are used together with eight landmarks, left and right foot, knee, hip joint and shoulder, in the image registrations. The objects relate to the landmarks according to Table 1.

TABLE 1

Landmark used for each body part/bone section in the registration method.

| Object | Landmarks |
|---|---|
| 1, left lower leg | left foot and knee |
| 2, right lower leg | right foot and knee |
| 3, left upper leg | left knee and hip |
| 4, right upper leg | right knee and hip |
| 5, pelvis | left and right hip |
| 6, torso | left and right hip and shoulder |
| 7, left upper arm | left shoulder |
| 8, head | left and right shoulder |
| 9, right upper arm | right shoulder |

To obtain a reliable bone registration, an initial deformation may be obtained by a similarity transform. The initial transform may be obtained by Procrustes analysis of the eight landmarks. The initial transform can be followed by a piecewise affine transform for each of the segmented and labeled bone sections together with the one, two or four closest landmarks, see Table 1.

For the spine, the four closest landmarks are used and a slightly elastic deformation can be allowed to compensate for different articulations of the spine.

Separate registration procedures for bone section 1-9 are now described. For each bone section k, a linear combination of the mean square distance between the fixed and the moving images, the mean square distance of distance transformed fixed and moving bone images and the mean Euclidean distance between the landmarks in the fixed and moving image.

A distance transform (DT) may assign the distance to the closest object voxel to each background voxel.

The pairs of landmarks used correspond to the landmarks, as given in Table 1, in the fixed and moving images.

A cost function may be minimized for an affine transform for all objects except the spine $k \neq 5$ for which a deformable transform (a B-spline grid with spacing 64 mm) may be used.

A multi-scale approach with a Gaussian pyramid (with $\sigma=4$ voxels, $\sigma=2$ voxels, no smoothing) and down sampling (with factor 4,2,1 in each dimension) may be used. To achieve a stable and precise registration, the contribution of the DT is high for the low resolutions (for stability) and low for the highest resolution.

Two sets of landmark pairs may be computed for each k bone section:
LMbone: For each bone section deformed by an affine (or elastic for the spine) deformation, a large number of corresponding points pairs in the fixed and moving images may be generated.
LMWB: Each body part may be deformed by the deformation given by the registration of the corresponding bone section. This deformation can be represented by a large number of landmarks, i.e., corresponding point pairs, in the fixed and moving images.

The landmarks (LMbone) may be used in future processing steps to constrain the deformation in the bone sections and the landmarks LMWB will be used for whole-body approximate registration described in the next section.

Figure 6:
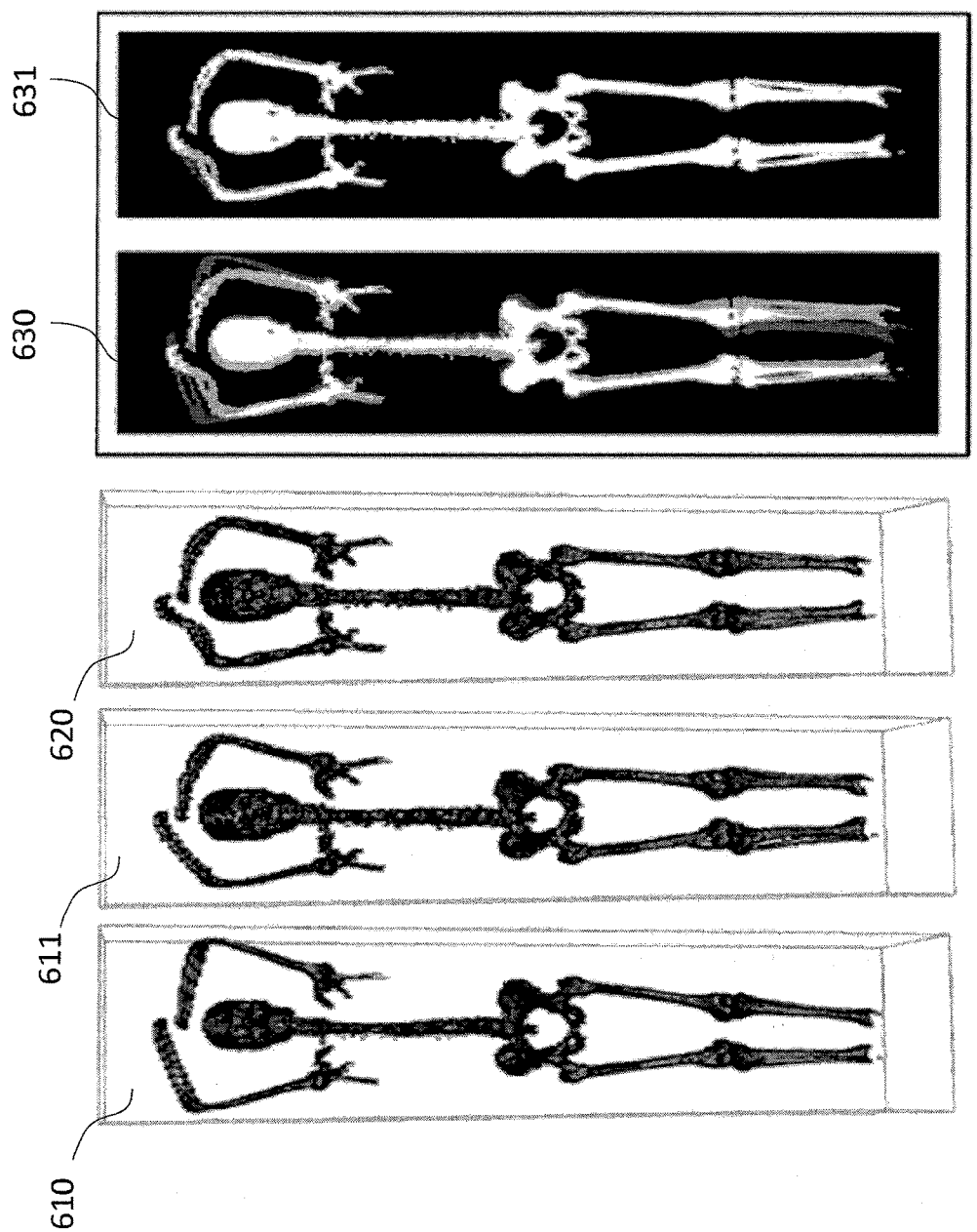
FIG. 6 illustrates bone registration, according to embodiments of the present disclosure.

FIG. 6 illustrates bone registration between two whole bodies collected from the same subject at two different time points. This figure illustrates a moving (or movable) image 610 and a deformed moving image 611. In 620 a fixed image being a reference onto which the moving image 610 is being mapped to create the deformed moving image 611 is shown. The symmetric difference between the bone images is also shown before 630 and after 631 the deformation, respectively. Deviations between the moving image and the fixed image are thus illustrated in 630 and 631 in grey. In 631 a significantly enhanced overlap and only minor deviations are shown, as compared to what is shown in 630.

The local deformations of the bones may be propagated to the whole body and represented by a smooth deformation field by computing a global deformation that minimizes the point-pair distances of $LM_{WB}$. In this step, the cost function may be a linear combination of the mean square distance between the fixed and the moving body mask images and the mean Euclidean distance between the landmarks $LM_{WB}$ in the fixed and moving image.

A deformable transform given by a B-spline grid with spacing 100 mm together with a multi-scale approach with a Gaussian pyramid (with σ=4 voxels, σ=2 voxels, no smoothing) and down sampling (with factor 4,2,1 in each dimension) may be used.

Water images may be registered by minimizing the sum of square differences of the water images and using the global deformation as presented above as initial transform and $LM_{BONE}$ as landmarks.

In this step, the cost function may be a linear combination of the mean square distance between the fixed and the moving water images and the mean Euclidean distance between the landmarks $LM_{WB}$ in the fixed and moving image.

A deformable transform given by a B-spline grid with spacing 64 mm together with a multi-scale approach with a Gaussian pyramid (with σ=4 voxels, σ=2 voxels, no smoothing) and down sampling (with factor 4,2,1 in each dimension) may be used. This provides an approximately correct position of lean tissue, muscles etc.

Pairs of matching points from the so-obtained water registration, $LM_{WATER}$ may be computed in voxels with high (>50%) water signal.

To achieve a final global registration, the mean square error of body masks and fat images may be minimized by $LM_{WATER}$ and $LM_{BONE}$ as landmarks. In this step, the cost function is a linear combination of the mean square distance between the fixed and the moving fat images, the mean square distance between the fixed and the moving body mask images and the mean Euclidean distance between the landmarks $LM_{WB}$ in the fixed and moving image.

A deformable transform given by a B-spline grid with spacing 32 mm together with a multi-scale approach with a Gaussian pyramid (with σ=2 voxels, no smoothing) and down sampling (with factor 4,2,1 in each dimension) may be used.

In a particular embodiment, the first image and the second image are images of one and the same whole body acquired at different times.

Each volume image may be associated with volume image features, enabling statistical analysis of said volume image features of various volume images.

The method may further comprise storing the registered first images, repeating the identifying, the registering and the storing of the registered first images. This repetition generates a group of multiple first images, which together form an atlas of stored volume images. This will be further discussed below. The storing of the registered first image may also comprise storing of image features of the first images. The image features may comprise one or more of following: volume image intensity values, calculated values based on volume image intensity values, and properties of the volume deformation field of each of the first images.

The invention thus enables, among other aspects, the creation of a statistical atlas being a statistical representation of image features such as tissue morphology, and characteristics as function and metabolism in all voxels of a studied whole body.

Figure 7:
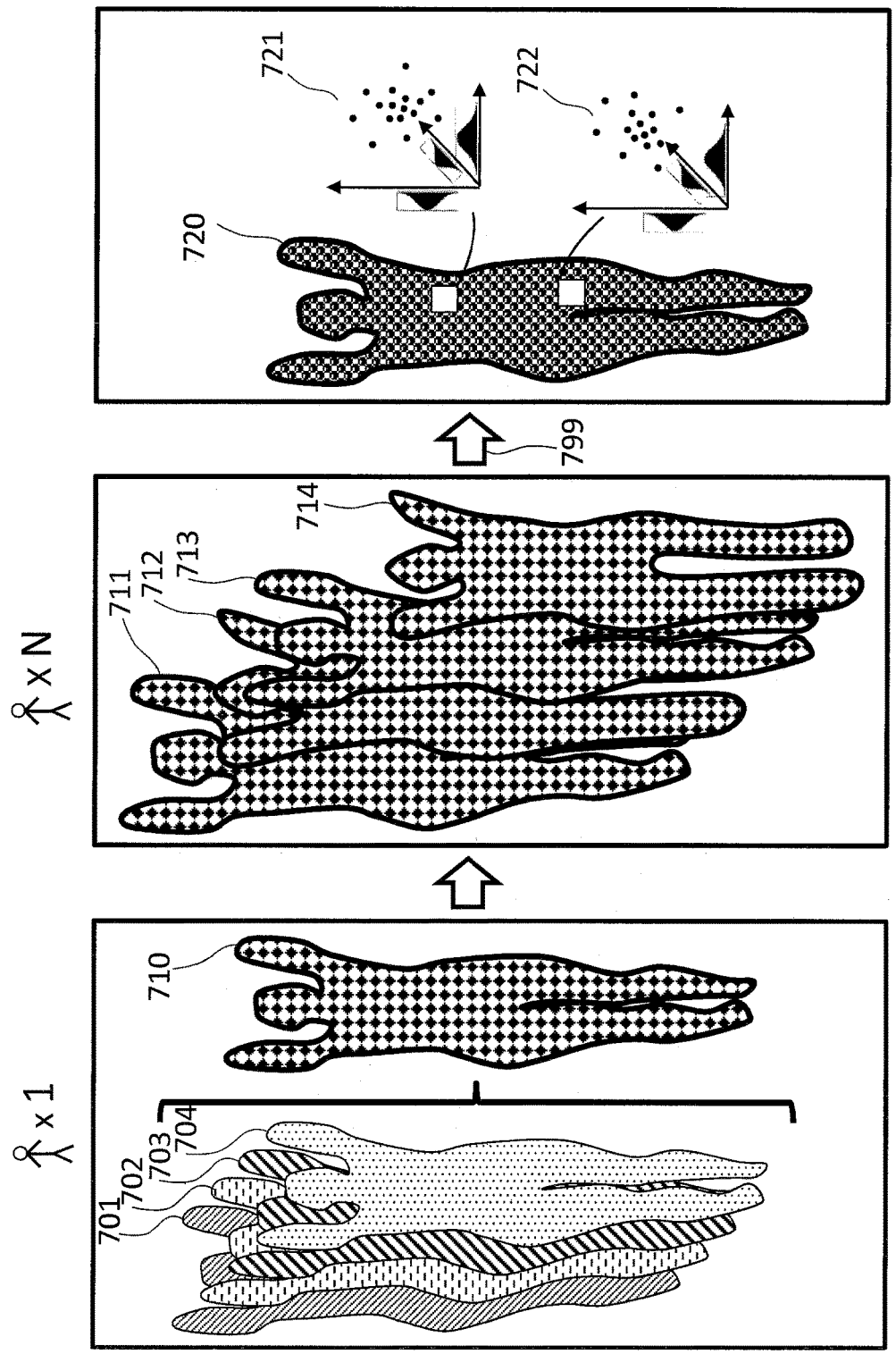
FIG. 7 illustrates an example of a statistical atlas.

FIG. 7 illustrates an example of a statistical atlas, related to embodiments of the present disclosure. This example statistical atlas is generated via fusion of PET and different MRI source images and calculated images from healthy subjects (bodies) into a common reference coordinate system, i.e. registering said images. The thereby created atlas then holds statistics of all image features included, i.e. morphology, function and metabolism.

In 701-704, the different kinds of whole body images, e.g. PET and different MRI source images from one subject, are combined into a common whole body image 710. All the different information carried by the individual images are conserved and are thus present also in the combined image 710. In 711-714 whole body images of many subjects are illustrated. The ensemble of whole body images could e.g. represent a group of healthy subjects, or a statistically selected group of subjects. The ensemble of whole body images are brought into a common reference coordinate system, i.e. registering 799 of the whole body images. The total image becomes an atlas 720 based on volume images of multiple bodies. In a preferred embodiment, the atlas comprises at least an intensity averaged and shape information averaged volume image based on said volume images of said multiple bodies.

By applying an image registration process, image data from a large number of healthy subjects (whole bodies) can be deformed to a common coordinate system to create a mean shape or reference person in which each voxel may be considered to contain a distribution of all imaging parameters 720-722 measured in an entire cohort of individuals.

The analysis of images is typically based on multispectral image data collected from different subjects (whole bodies) or at different points in time. This approach may be used to combine whole-body image data from, for instance, healthy subjects to create a statistical atlas that contains detailed statistics on tissue morphology, function, and metabolism in all voxels in the entire body.

By using the atlas, image data from each individual dataset may then be compared to this statistical atlas, in order to calculate deviations in each pixel from all image parameters collected, such as fat and water content, FDG-uptake, etc. in the entire body, as illustrated by the diagrams in part C of FIG. 7.

The image registration as described herein allows in general words point-to-point, tissue-to-tissue and organ-to-organ analysis.

Figure 8:
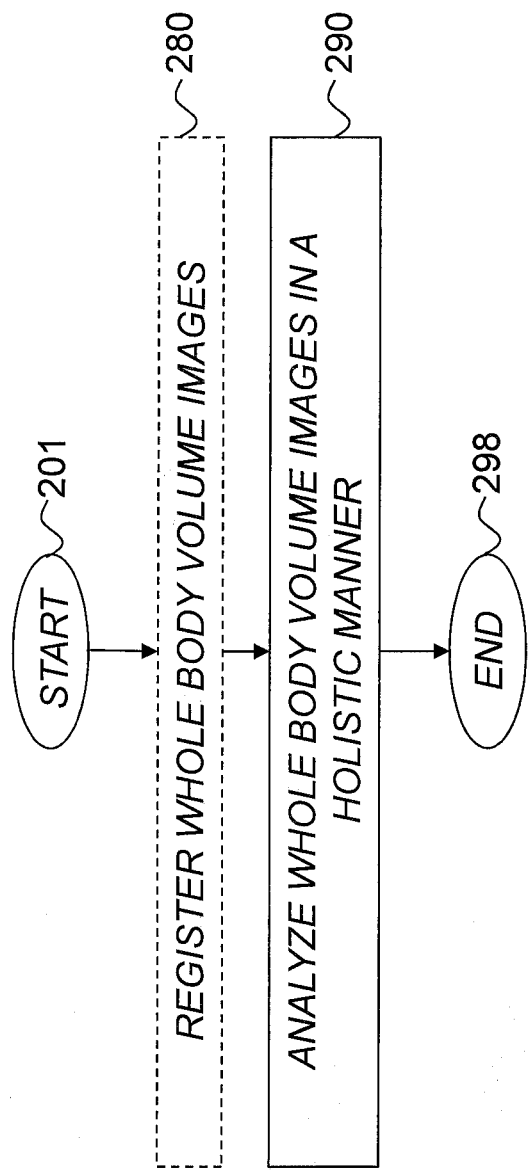
FIG. 8 is a flow diagram of steps of an embodiment of a method for analysis of whole body volume images.

FIG. 8 is a flow diagram of steps of an embodiment of a method for analysis of whole body volume images. The method starts in step 201. In step 290, image features of whole body volume images obtainable by a registering method according to the description here above are analysed in a holistic manner. The image features comprise one or more of signal intensities, features derived from a deformation field, and filtered measures derived from imaging parameters and optionally also from non-imaging parameters in all voxels. The procedure ends in step 298.

In a particular embodiment, illustrated with broken lines in FIG. 8, the method comprises the further step 280, in which whole body volume images are registered according to the principles described elsewhere in this disclosure. The step of analysing image features is then based on registered whole body volume images obtained by this step 280.

Embodiments of the present disclosure may be used for a number of different studies of whole bodies, of which three major categories will be described below.

Figure 9:
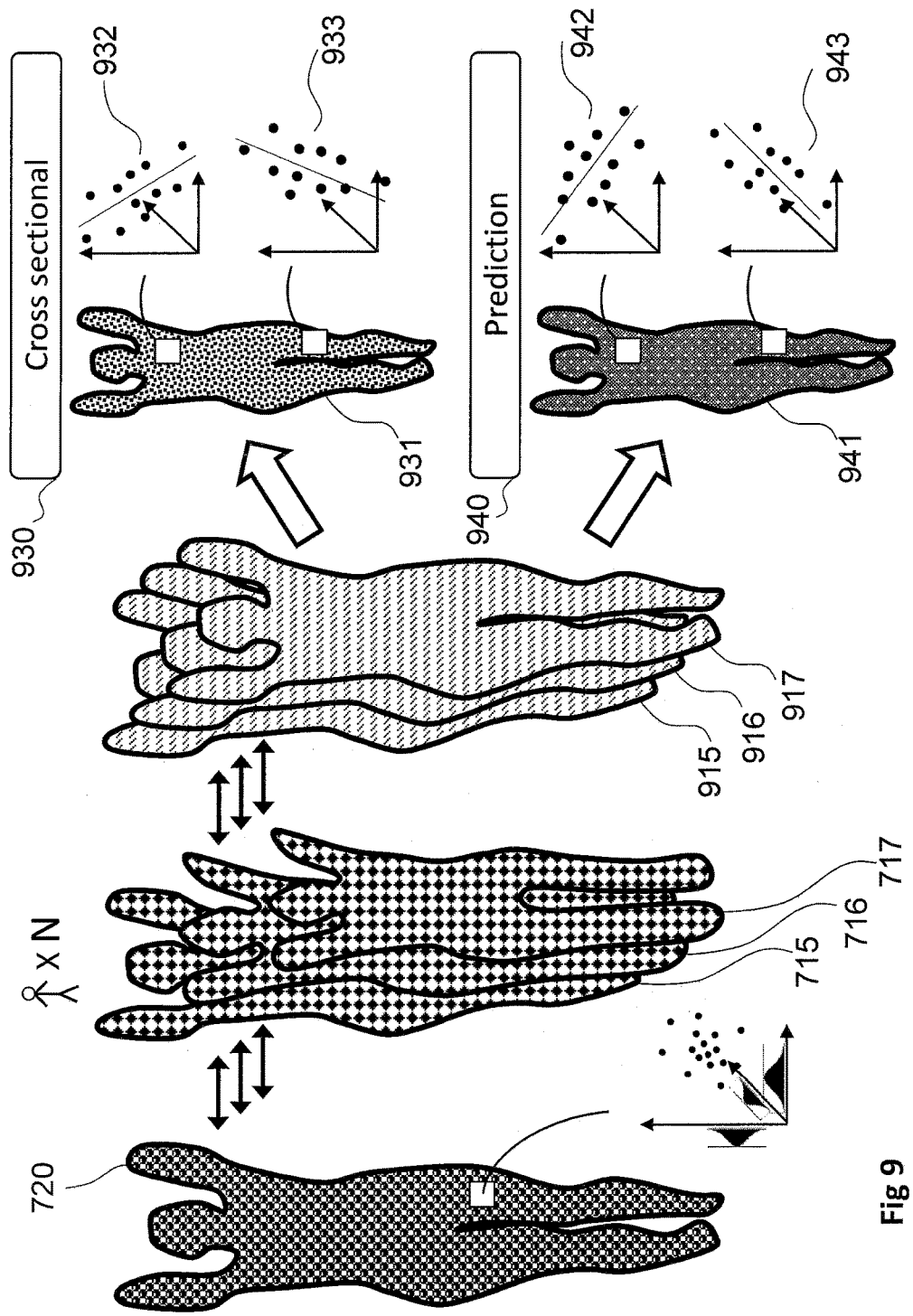
FIG. 9 presents an illustration of one embodiment using results from image registration in a method for image analysis.

FIG. 9 presents an illustration of some embodiments using results from image registration in a method for image analysis. In this figure the image analysis comprises cross-sectional 930 studies and prediction 940 cohort studies. The figure illustrates how an atlas 720 can be used to assess deviations 915-917 in image parameters in whole body images 715-717 and study their associations to non-imaging data 930-933 and 940-943.

In cross-sectional studies 930-933, associations to scalar valued parameters may be studied. In cross-sectional studies imaging data is typically collected from one point in time, and non-imaging parameters are collected from the same point in time. Non-image parameters may comprise blood samples. Cross-sectional studies may be studied using whole-body "correlation-maps", and groups of subjects, for instance normal versus pre-diabetic, can be compared using whole-body "difference-maps".

In one embodiment, the step of analyzing image features thus comprises a cross-sectional analysis, analyzing a multitude of whole body volume images from more than one whole body. In a particular embodiment, the cross-sectional analysis comprises collected non-imaging data associated with whole bodies of the whole body volume images. In a particular embodiment, the step of analyzing image features comprises calculating of a correlation between image features of a group of whole body volume images with said collected non-imaging data.

Prospective studies for risk prediction 940-943 may further be used to create "prediction-maps" 941 of what whole-body tissue features predict "time to event" or the future risk of, for instance, type-2 diabetes, myocardial infarction, stroke or dementia, respectively. In prediction, imaging data is collected at one point in time, whereas non-imaging data is typically collected at a later point in time.

Figure 10:
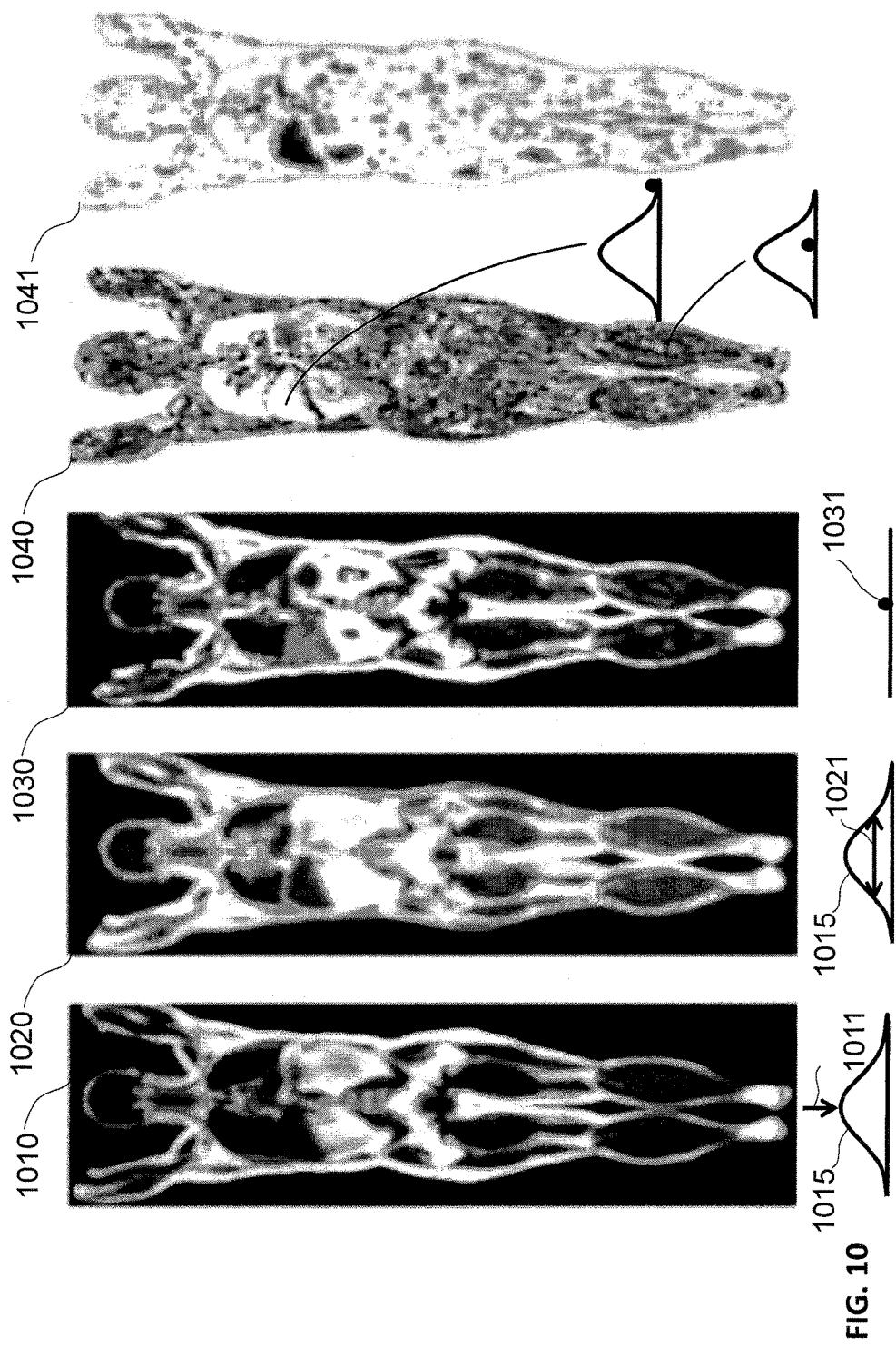
FIG. 10 presents results from atlas creation and application for anomaly detection.

FIG. 10 illustrates the results from atlas creation and anomaly detection. The anomaly detection was performed by comparing intensities of one male subject with high liver fat content 1030 to a preliminary whole body imaging atlas 1010 and 1020, i.e. pointwise distributions 1015 of fat content of 50 male subjects. The results indicate low p-values where expected, i.e. in the abdominal adipose tissue and in the liver, respectively 1040. A coronal example slice is shown from each whole body image volume.

Mean 1011 absolute fat content in the normal material (atlas) is show in 1010. Values from 0% (black) to 100% (white).

One standard deviation 1021 of absolute fat content in the normal material (atlas) is shown in 1020. Values from 0% (black) to 40% (white).

Absolute fat content 1031 in a male subject with high liver fat is shown in 1030. Values from 0% (black) to 100% (white).

Pointwise p-values of the hypothesis that the fat content in the male subject with high liver fat does not differ from the normal material are shown in 1040. Values from 0 (white) to 1 (black).

Pointwise p-values of the hypothesis that the fat content in the male subject with high liver fat does not differ from the normal material thresholded at 0.05 are shown in 1041. Points with p-values below 0.05 are black and the rest white.

In an embodiment, the step of analyzing image features thus comprises comparing a whole body volume image from one whole body with an atlas.

Figure 11:
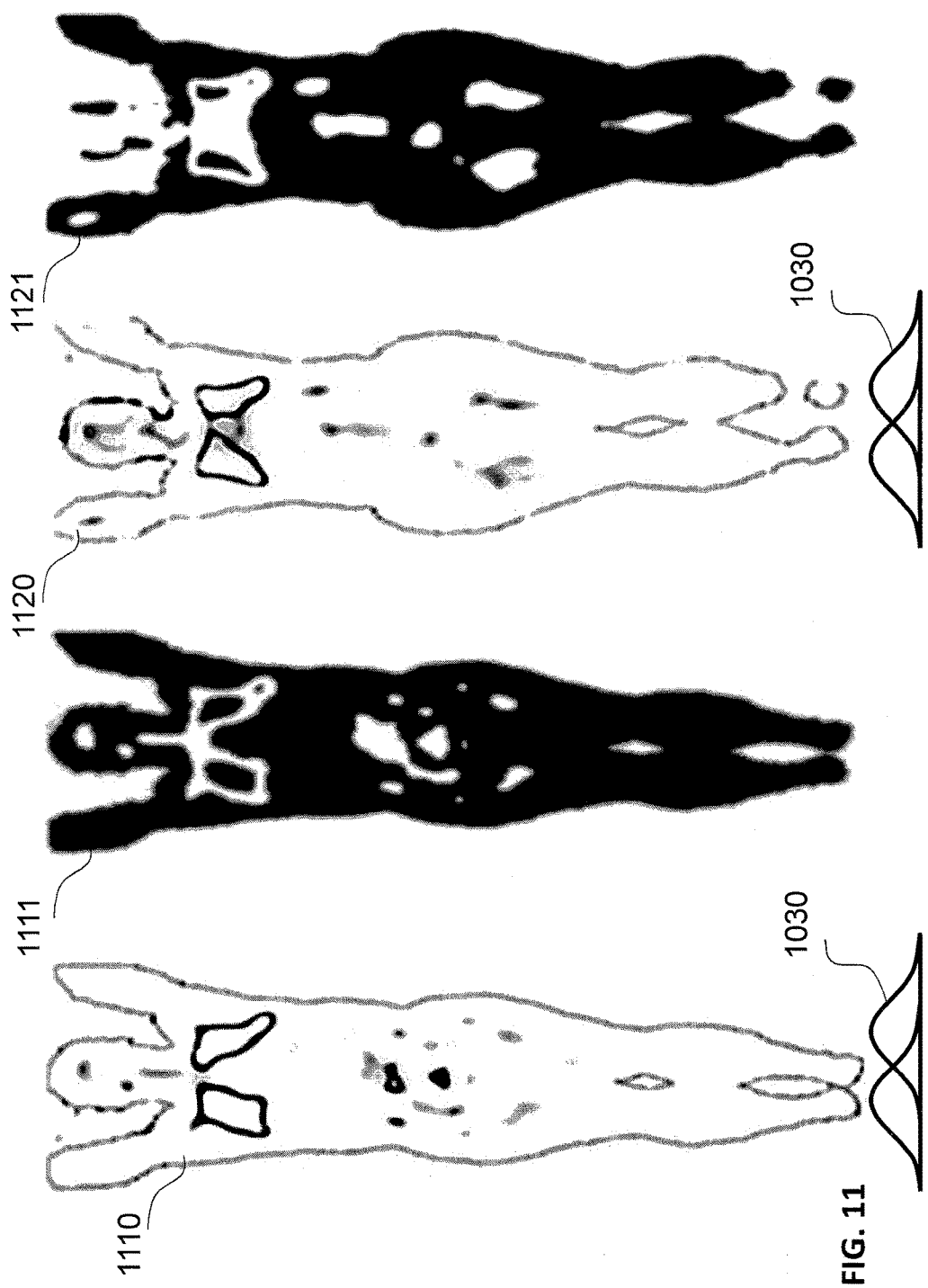
FIG. 11 presents results from whole body comparisons between different groups of subjects.

FIG. 11 shows the point-by-point p-values (p-maps) of local tissue volume were obtained by two-tailed t-tests between groups 1030 of low weight subjects and high weight subjects (20 men and 23 women). As expected, significant differences of local tissue volume (size) were observed between the two groups. A coronal example slice is shown from each whole body image volume.

p-maps are shown for male 1110 and female 1120. Values from 0 (white) to 1 (black).

p-maps thresholded at 0.05 for male 1111 and female 1121 are also shown. Significant p-values are shown in black.

In an embodiment, the step of analyzing image features thus comprises comparing a first group of body volume images to a second group of body volume images.

Figure 12:
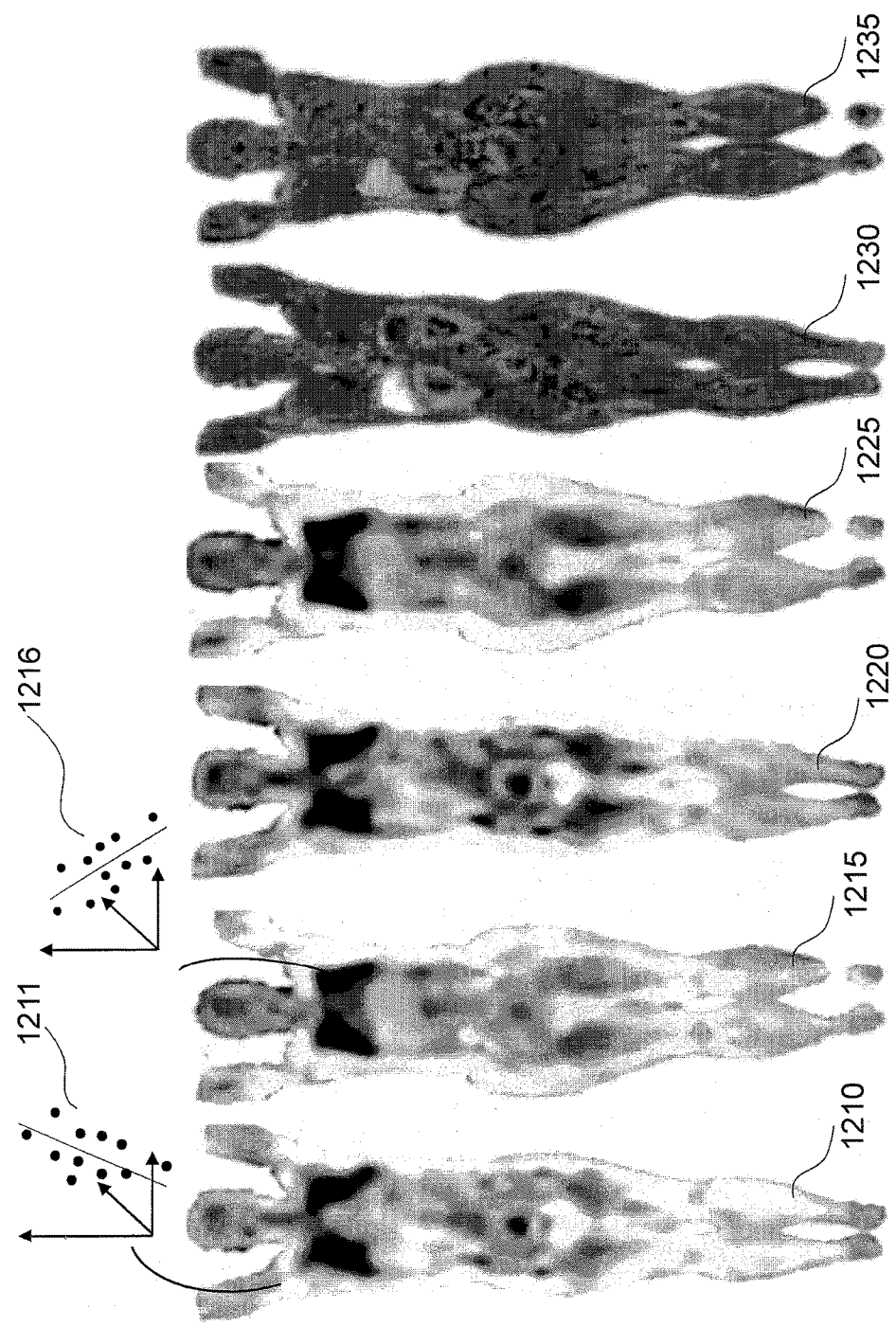
FIG. 12 presents results from cross sectional correlations studies between different imaging data features and non-imaging data.

FIG. 12 shows cross-sectional analysis results from of male (n=60) and female (n=68) subjects. Maps with point-wise correlation 1211, 1216 (r-value) between local tissue volume and weight, local tissue volume and total body fat mass measured by bioimpedance analysis (BIA) and fat content and mean liver fat content. Values from −1 (black) to 1 (white). A coronal example slice is shown from each whole body image volume.

The figure shows pointwise r-values between local tissue volume and body weight in males 1210 and females 1215.

The figure shows pointwise r-values between local tissue volume and total body fat mass measured by bioimpedance analysis (BIA) in males 1220 and females 1225.

The figure shows pointwise r-values between fat content and mean liver fat content in males 1230 and females 1235.

These examples show the correlation to non-imaging measurements where we know what results to expect; (1210, 1215,1220,1225) the correlations in adipose tissue are positive and strong while correlations in other tissues are weaker and agree well with explicitly measured volumes from MRI and (1230,1235) explicit measurements of liver content agree with fat content from image data.

Figure 13:
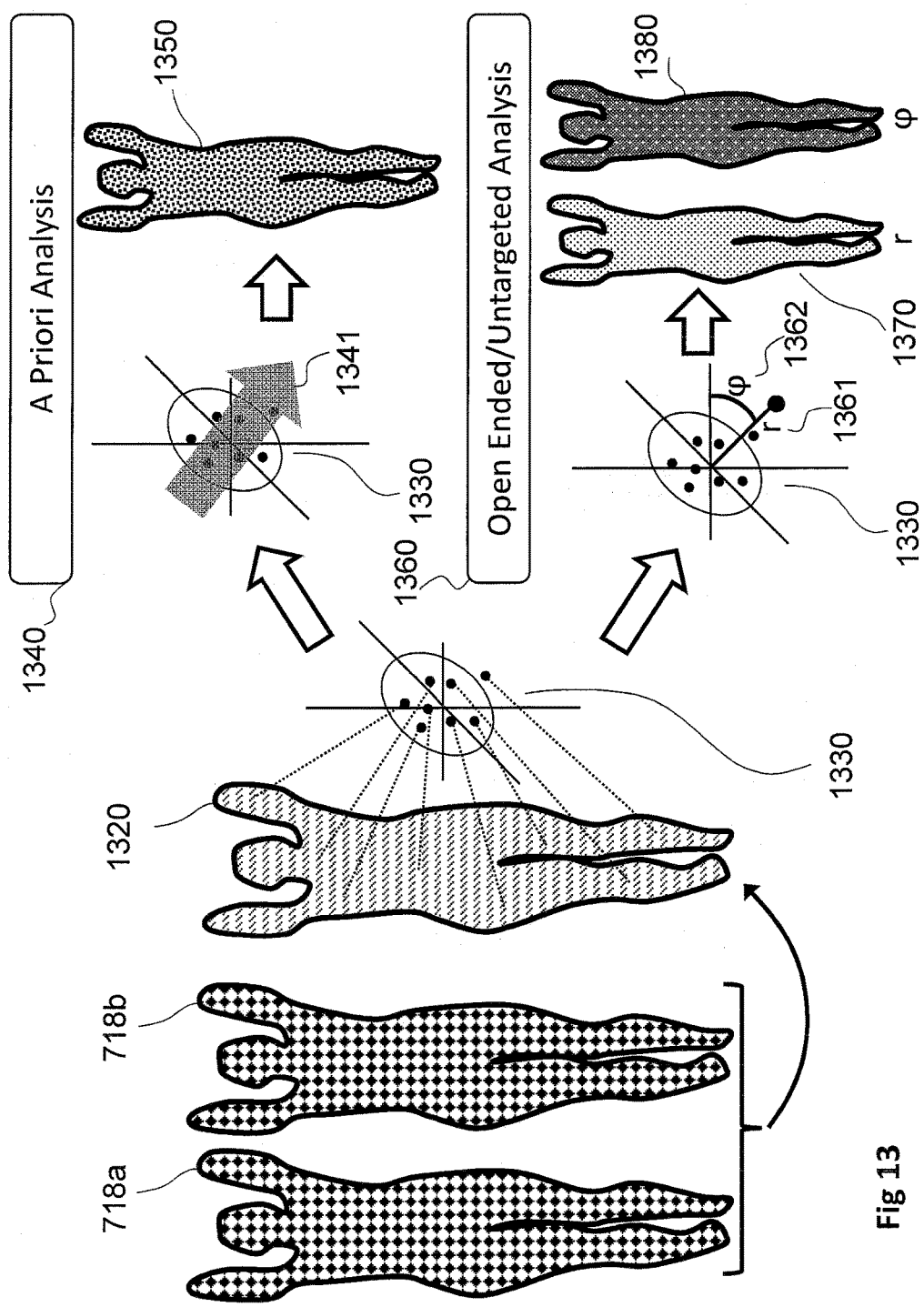
FIG. 13 presents an illustration of another embodiment using results from image registration in a method for image analysis.

FIG. 13 presents an illustration of some embodiments using results from image registration in a method for a longitudinal image analysis. Longitudinal studies may be used for detailed studies of changes in tissue feature during, for example, oncological or diabetes treatment. In longitudinal studies, image data as well as non-imaging data can be collected at multiple points in time 718a and 718b. The registration of these images can result in a difference image 1320 which contains changes in the different image features 1330 in the whole body region between the time points.

The analysis of the image data may be generalized into categories. One category being, a priori driven 1340, i.e. based on a hypothesis 1341 and 1350, and another being open ended 1360, i.e. general search for feature deviations 1361, 1362, 1370, 1380. The arrow 1341 illustrates the hypothesized a priori direction of change. Using statistics of changes in image features the r-value illustrated 1361 can be converted into a p-value of statistical significance of the feature change.

Figure 14:
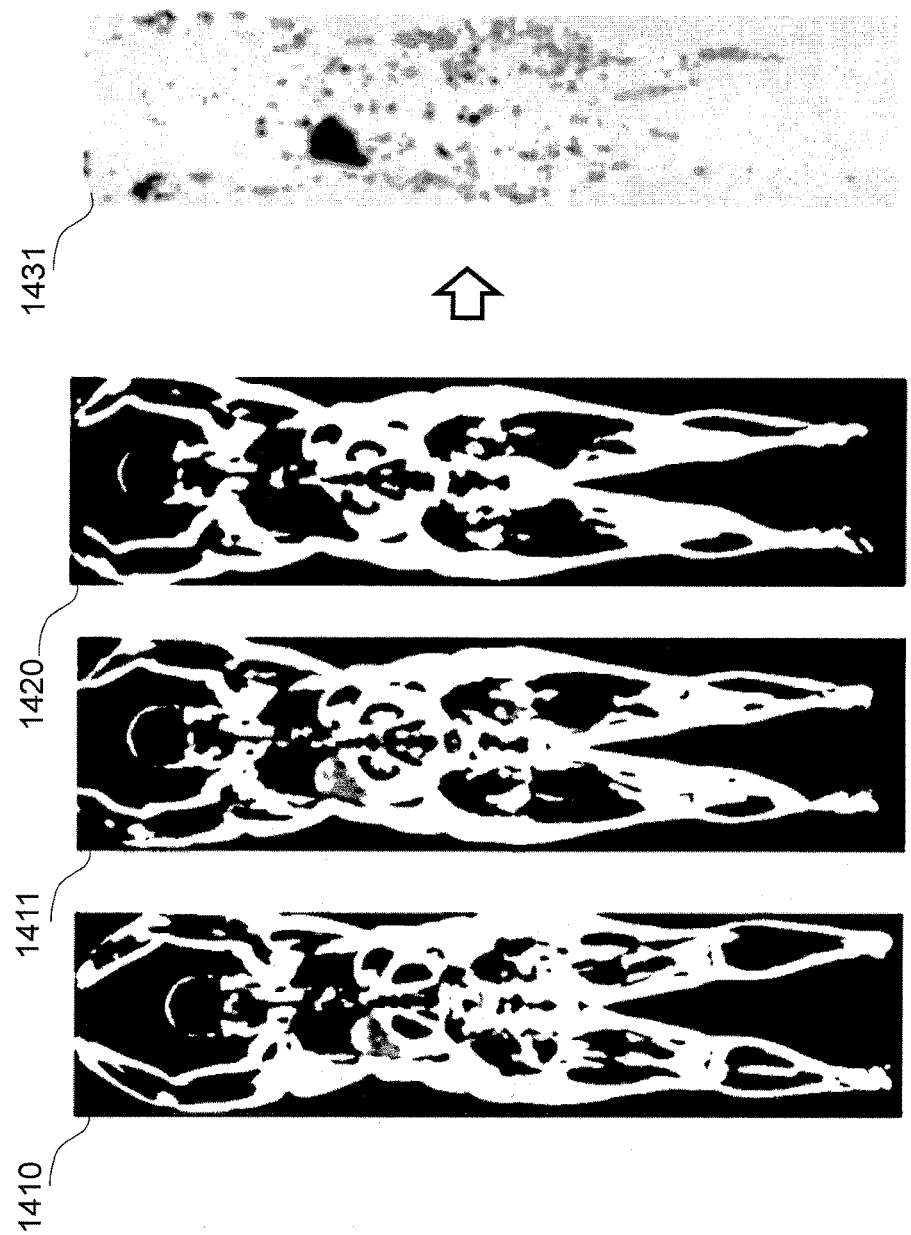
FIG. 14 presents an example result from a longitudinal study.

FIG. 14 shows an example from a longitudinal study where the registration method is applied. One coronal slice of the moving 14010, deformed moving 1411 and fixed 1420 images of absolute fat content is shown together with a difference image 1431 between the fixed and deformed moving images. The moving image is deformed to match the fixed image using the described methodology. The subject underwent low calorie diet (LCD) and gastric bypass (GBP) between the moving and fixed MRI-scans. The total weight loss was 14 kg. Note the significant reduction in liver fat. This methodology could for example be used for "weight loss imaging", to visualize where and when volumetric and tissue property (e.g. intensity) changes occur or for studying changes in image features during for example cancer treatment. A coronal example slice is shown from each whole body image volume.

The figure shows absolute fat content in the baseline volume (moving) 1410. Values from 0% (black) to 100% (white).

The figure shows absolute fat content in the deformed baseline volume (moving) 1411. Values from 0% (black) to 100% (white).

The figure shows absolute fat content in the follow-up volume (fixed) 1420. Values from 0% (black) to 100% (white).

The figure shows a difference-image, i.e. the difference in absolute fat content between 1420 and 1411. Values from −20% (black) to 20% (white).

In an embodiment, the step of analyzing image features thus comprises a longitudinal analysis, analyzing differences between a multitude of whole body volume images from one and the same whole body acquired at different times.

In a particular embodiment, the step of analyzing image features is based on a hypothesis.

In another particular embodiment, the step of analyzing image features is based on a general search for feature deviations.

The statistical interaction between image features and non-imaging parameters may be studied in the whole-body region using different approaches.

One approach being correlations, such as correlation maps between image features and insulin resistance.

Another approach being group-wise comparisons, where associations in image features between two groups of whole body images are studied. The groups are typically divided by non-imaging parameters. For example, to create a voxel-level statistical test of feature difference between two groups of individuals, e.g. normal versus type-2-diabetics, etc.

Another approach is multivariate modelling, where different statistical models, such as linear, logistic, Cox hazard, factor analysis, lasso, boosted regression trees, can include multiple variables, e.g. age/blood pressure/smoking/physical activity in the analysis.

Still another approach being anomaly detection, where differences in image features between an imaging atlas, or group of normality, and a subject with suspected non-normality referring to image features or non-imaging parameters, are studied.

Still another may be considered to be cross-sectional analysis where associations between image features and non-imaging parameters in a statistical whole body atlas, or group of whole body images, are studied.

Still yet another approach is the longitudinal analysis, where changes/differences in image features in whole body images of the same individual acquired at different time-points, are studied.

Also, attenuation correction may be considered to be one approach. Segmentation, or detection of, of tissue, such as bone, water, fat and pre-segmented organs, by utilizing an imaging atlas holding pre-segmented tissue, provides information to be used in attenuation correction needed in PET-MR imaging.

Throughout this disclosure image features, wherever mentioned may comprise one or more of signal intensities, features derived from a deformation field, typically regional volumes, and filtered measures, such as texture, segmented tissue.

As mentioned above, this disclosure aims at using the full potential of image data by avoiding reducing image information to a few measures or parameters, and by carrying out a holistic analysis on each image, and on large numbers of collected images by a statistical representation and also by allowing integration of non-imaging biomarkers in an analysis of images.

Embodiments herein described are based on an image registration method which uses tissue-specific handling of fat/water MR images and pre-segmented bone.

Previous methods for image registration of fat/water MR images have not been able to use tissue-specific properties of pre-segmented bone, lean, and adipose tissue. Approaching the challenging problem of whole body fat/water MR image registration by multi-atlas methods has until now not given a one-to-one correspondence between two images, but a probability map giving the probability for each point to belong to each of the segmentation classes. Since the deformation field has not been readily available, statistical analysis that require one-to-one correspondences could not be performed by multi-atlas approaches.

FIG. 15 schematically illustrates a method for image analysis, according to some embodiments.

In 51, the method comprises performing a comparison of where and how image features, or image features derived from a deformation field, of the method for registration of volume images of whole bodies differ within a first group of first sets of volume images and within a second group of first sets of volume images, wherein said first and said second group of first sets of volume images are comprised within the atlas of volume images.

In 52, the method alternatively comprises calculating a correlation between image features, or image features derived from a deformation field, of the method for registration of volume images of a group of first sets of volume images of whole bodies of the volume image atlas and collected non-imaging data associated with said whole bodies comprising one or more of: blood pressure or measurement results from blood analysis, measurement results from non-imaging analysis, biomarkers or data from longitudinal studies of disease development.

In 53, the method alternatively comprises performing a comparison of image features, or image features derived from a deformation field, of the method for registration of volume images from a set of registered volume images of a whole body and a volume image atlas of registered volume images of multiple whole bodies enabling detecting where and how image features from a whole body deviate from image features from multiple whole bodies of the atlas of volume images.

In 54, the method alternatively comprises using the method for registration of volume images to identify bone tissue and at least one other tissue of the volume images, enabling tissue quantification in MR-type imaging or improving attenuation correction in PET-MR imaging.

In 55, the method alternatively comprises performing comparisons of where and how image features differ between sets of registered volume images of one and the same whole body acquired at different time points.

It should be clarified that although the method for image analysis as presented above, has been presented as alternative methods or sub methods, this does not prevent the method to comprise two or more of said sub methods 51, 52, 53, 54 and 55.

Advantages of embodiments of the present disclosure comprise:

Whole body image registration is made possible by utilizing fat-water MRI images, which enables automatic segmentation of tissue into regions with different elasticity properties. The use of tissue-dependent registration rules allows robust image registration.

Figure 16:
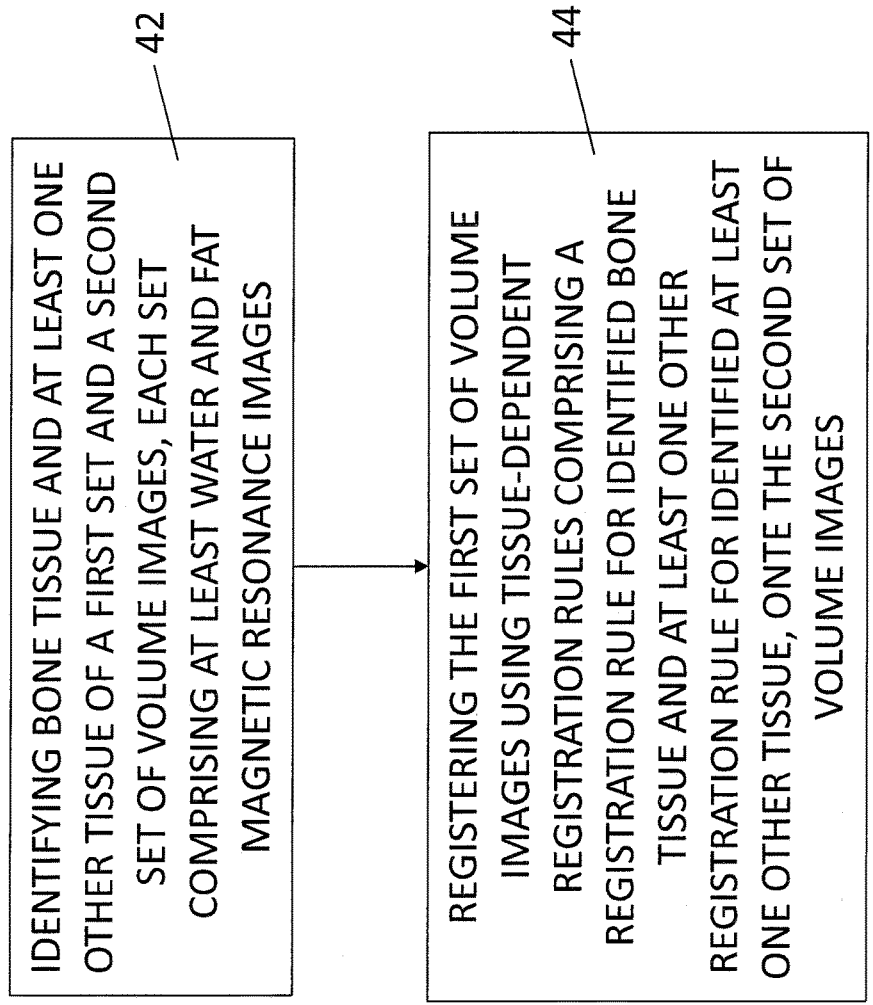
FIG. 16 presents a flow chart illustrating a method for registration of volume images.

FIG. 16 presents a flow chart illustrating a method for registration of volume images of one or more whole bodies. The method comprises identifying 42 bone tissue and at least one other tissue of a first set and a second set of volume images, each set of volume images comprising at least water and fat MR images. The method also comprises registering 44 one or more of the first set of volume images, onto the second set of volume images, using tissue-dependent registration rules comprising a registration rule for bone tissue and at least one other registration rule for said at least one other tissue, based on identified bone tissue and identified at least one other tissue.

The tissue-dependent registration rules in registering one or more of the first set of volume images, may comprise tissue-dependent deformation rules, and registering one or more of the first set of volume images, may comprise deforming bone tissue of said one or more of the first set of volume images using a bone tissue deformation rule and deforming said at least one other tissue of said one or more of the first set of volume images using at least one other tissue deformation rule.

The tissue-dependent deformation rules may comprise tissue-dependent elasticity rules, specifying rules of tissue-dependent elasticity, and deforming bone tissue may comprise deforming bone tissue using a bone tissue elasticity, and deforming said at least one other tissue may comprise deforming said at least one other tissue using at least one other tissue elasticity.

The tissue-dependent elasticity rules may further comprise a pre-dominantly water-containing tissue elasticity, and predominantly fat-containing tissue elasticity, wherein the bone tissue elasticity is lower than the water-containing tissue elasticity that is lower than the fat-containing tissue elasticity.

Registering said one or more of the first set of volume images onto the second set of volume images within the method may comprise deforming bone tissue of said one or more of the first set of volume images, prior to deforming predominantly-water containing tissue of said one or more of the first set of volume images, prior to deforming predominantly fat-containing tissue of said one or more of the first set of volume images.

A reference to an element in the singular is not intended to mean "one and only one" unless explicitly so stated, but rather "one or more." All structural and functional equivalents to the elements of the above-described embodiments that are known to those of ordinary skill in the art are expressly incorporated herein by reference and are intended to be encompassed hereby.

In the preceding description, for purposes of explanation and not limitation, specific details are set forth such as particular architectures, interfaces, techniques, etc. in order to provide a thorough understanding of the disclosed technology. However, it will be apparent to those skilled in the art that the disclosed technology may be practiced in other embodiments and/or combinations of embodiments that depart from these specific details. That is, those skilled in the art will be able to devise various arrangements which, although not explicitly described or shown herein, embody the principles of the disclosed technology. In some instances, too detailed descriptions of methods or principles are omitted so as not to obscure the description of the disclosed technology with unnecessary detail. All statements herein reciting principles, aspects, and embodiments of the disclosed technology, as well as specific examples thereof, are intended to encompass both structural and functional equivalents thereof. Additionally, it is intended that such equivalents include both currently known equivalents as well as equivalents developed in the future, e.g. any elements developed that perform the same function, regardless of structure.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

Abbreviations

ADC apparent diffusion coefficient

CPU central processing unit

CT computed tomography

DT distance transform

FDG fluorodeoxyglucose

GPU graphical processing unit

LM landmark

MR magnetic resonance

MRI MR imaging

SDD sum of squared differences

SPM statistical parameter mapping

VBM voxel-based morphometry

References

1. Ashburner, J.; Friston, K. J., Voxel-based morphometry—the methods. Neuroimage 2000, 11 (6), 805-821.

2. Aerts, H. J. W. L.; Velazquez, E. R.; Leijenaar, R. T. H.; Parmar, C.; Grossmann, P.; Carvalho, S.; Bussink, J.; Monshouwer, R.; Haibe-Kains, B.; Rietveld, D.; Hoebers, F.; Rietbergen, M. M.; Leemans, C. R.; Dekker, A.; Quackenbush, J.; Gillies, R. J.; Lambin, P., Decoding tumour phenotype by noninvasive imaging using a quantitative radiomics approach. Nat Commun 2014, 5.

3. Gupta, A.; Krishnan, A.; Zhou, X. S., Systems and Methods for Computer Aided Diagnosis and Decision Support in Whole-Body Imaging, U.S. Pat. No. 8,588,495 B2. 2013.

4. Poole, I. Image processing method and system, Patent document US2013/0044927 A1.

5. Joshi, A. A.; Hu, H. H.; Leahy, R. M.; Goran, M. I.; Nayak, K. S., Automatic intra-subject registration-based segmentation of abdominal fat from water-fat MRI. Journal of Magnetic Resonance Imaging 2013, 37 (2), 423-430.

6. Karlsson, A.; Rosander, J.; Romu, T.; Tallberg, J.; Gronqvist, A.; Borga, M.; Dahlqvist Leinhard, O., Automatic and quantitative assessment of regional muscle volume by multi-atlas segmentation using whole-body water-fat MRI. J Magn Reson Imaging 2014.

The invention claimed is:

1. A method for registration of whole body volume images, the method comprising the steps of:

obtaining a first image and a second image;

said first image being a whole body volume image comprising water and fat magnetic resonance image data and said second image being a whole body volume image comprising water and fat magnetic resonance image data;

identifying bone tissue from said first image creating a first bone image, and identifying bone tissue from said second image creating a second bone image;

separating water components from said first image, generating a first water image based on absolute water content, and separating water components from said second image, generating a second water image based on absolute water content;

separating fat components from said first image, generating a first fat image based on absolute fat content, and separating fat components from said second image, generating a second fat image based on absolute fat content; and registering said first image to said second image by deforming said first bone image according to a bone tissue deformation rule, deforming said first water image according to a water tissue deformation rule under constraints of said deformation of said first bone image and deforming said first fat image according to a fat tissue deformation rule under constraints of said deformation of said first bone image and said deformation of said first water image.

2. The method according to claim 1, wherein said bone tissue deformation rule comprises a bone tissue elasticity, said water tissue deformation rule comprises a water-containing tissue elasticity and said fat tissue deformation rule comprises a fat-containing tissue elasticity, wherein said bone tissue elasticity is lower than said water-containing tissue elasticity and said water-containing tissue elasticity is lower than said fat-containing tissue elasticity.

3. The method according to claim 1, wherein said deforming of said first bone image is performed prior to said deforming of said first water image, and said deforming of said first water image is performed prior to said deforming of said first fat image.

4. The method according to claim 1, wherein said step of registering comprises determining of a volume deformation field and applying said volume deformation field on said first volume image.

5. The method according to claim 1, wherein said step of registering comprises determining of a point-to-point correspondence between said first image and said second image.

6. The method according to claim 1, comprising the further step of identifying of a plurality of landmarks in said first image and in said second image, and in that said step of registering comprises matching of said identified plurality of landmarks between said first image and said second image.

7. The method according to claim 1, comprising the further step of segmenting said first image and said second image into segments, wherein said step of registering comprises matching of said segments between said first image and said second image.

8. The method according to claim 1, comprising the further steps of:

extracting a body mask from said water and fat magnetic resonance image data; and extracting body parts from said body mask;

wherein said step of registering is performed at least partly for each said body part.

9. The method according to claim 1, wherein at least one of said first image and said second image is further associated with collected non-imaging data.

10. The method according to claim 1, wherein said first image and said second image are images of one and the same whole body acquired at different times.

11. The method according to claim 1, further comprising repeating said method of registration for a multiple of first images.

12. The method according to claim 1, wherein said second image is an atlas based on volume images of multiple bodies.

13. A method for analysis of whole body volume images, the method comprising the step of:

analyzing image features of whole body volume images obtained by a registering method according to claim 1 in a holistic manner, said image features comprising one or more of signal intensities, features derived from a deformation field, and filtered measures derived from imaging parameters and optionally also from non-imaging parameters in all voxels.

14. A method for analysis of whole body volume images, the method comprises the steps of:

registering whole body volume images according to claim 1; and analyzing image features of whole body volume images obtained by the step of registering in a holistic manner, said image features comprising one or more of signal intensities, features derived from a deformation field, and filtered measures derived from imaging parameters and optionally also from non-imaging parameters in all voxels.

15. The method according to claim 13, wherein said step of analyzing image features comprises a cross-sectional analysis, analyzing a multitude of whole body volume images from more than one whole body.

16. The method according to claim 15, wherein said cross-sectional analysis comprises collected non-imaging data associated with whole bodies of said whole body volume images.

17. The method according to claim 16, wherein said step of analyzing image features comprises calculating of a correlation between image features of a group of whole body volume images with said collected non-imaging data.

18. The method according to claim 15, wherein said step of analyzing image features comprises comparing a whole body volume image from one whole body with an atlas.

19. The method according to claim 15, wherein said step of analyzing image features comprises comparing a first group of body volume images to a second group of body volume images.

20. The method according to claim 13, wherein said step of analyzing image features comprises a longitudinal analysis, analyzing differences between a multitude of whole body volume images from one and the same whole body acquired at different times.

* * * * *